(12) United States Patent
Jain et al.

(10) Patent No.: US 12,048,691 B2
(45) Date of Patent: Jul. 30, 2024

(54) HIGH DOSAGE TEBIPENEM PIVOXIL TABLET FORMULATION

(71) Applicant: SPERO THERAPEUTICS, INC., Cambridge, MA (US)

(72) Inventors: Akash Jain, Cambridge, MA (US); Ching-Kuo Jim Chow, Cambridge, MA (US)

(73) Assignee: SPERO THERAPEUTICS, INC., Cambridge, MA (US)

(*) Notice: Subject to any disclaimer, the term of this patent is extended or adjusted under 35 U.S.C. 154(b) by 0 days.

(21) Appl. No.: 17/525,619

(22) Filed: Nov. 12, 2021

(65) Prior Publication Data

US 2022/0142986 A1 May 12, 2022

Related U.S. Application Data

(60) Provisional application No. 63/112,434, filed on Nov. 11, 2020.

(51) Int. Cl.

| A61K 9/20 | (2006.01) |
|---|---|
| A61K 31/427 | (2006.01) |
| A61P 31/04 | (2006.01) |

(52) U.S. Cl.
CPC .......... *A61K 31/427* (2013.01); *A61K 9/2009* (2013.01); *A61K 9/2027* (2013.01); *A61K 9/2054* (2013.01); *A61P 31/04* (2018.01)

(58) Field of Classification Search
None
See application file for complete search history.

(56) References Cited

U.S. PATENT DOCUMENTS

| 4,851,230 | A | 7/1989 | Tencza et al. |
|---|---|---|---|
| 5,534,510 | A | 7/1996 | Abe et al. |
| 5,886,172 | A | 3/1999 | Abe et al. |
| 2004/0037883 | A1 | 2/2004 | Zhou et al. |
| 2006/0099253 | A1 | 5/2006 | Becker et al. |
| 2008/0069879 | A1* | 3/2008 | Bhiwgade ............ A61K 31/545 514/202 |
| 2020/0016126 | A1 | 1/2020 | Jain et al. |
| 2020/0055857 | A1 | 2/2020 | Jain et al. |

FOREIGN PATENT DOCUMENTS

| CN | 102558181 A | 7/2012 |
|---|---|---|
| CN | 102836130 A | 12/2012 |
| CN | 102276611 B | 1/2013 |
| CN | 102860985 B | 1/2013 |
| CN | 102885811 B | 1/2013 |
| CN | 102952125 A | 3/2013 |
| CN | 103054815 A | 4/2013 |
| CN | 103371977 A | 10/2013 |
| CN | 103655483 A | 3/2014 |
| CN | 103664949 A | 3/2014 |
| CN | 104013583 A | 9/2014 |
| CN | 104027310 A | 9/2014 |
| CN | 104224725 A | 12/2014 |
| CN | 103664948 B | 12/2015 |
| CN | 105193742 A | 12/2015 |
| CN | 105963261 A | 9/2016 |
| CN | 105997891 A | 10/2016 |
| CN | 106543186 A | 3/2017 |
| CN | 108640920 A | 10/2018 |
| CN | 109096283 A | 12/2018 |
| CN | 109651372 A | 4/2019 |
| CN | 107737107 B | 5/2020 |
| EP | 0632039 A1 | 4/1995 |
| JP | 08256296 A | 10/1996 |
| JP | H10195076 A | 7/1998 |
| JP | 3317604 B2 | 8/2002 |
| JP | 3317649 B2 | 8/2002 |
| JP | 2003171277 A | 6/2003 |
| JP | 2004035517 A | 2/2004 |
| JP | 2004035518 A | 2/2004 |
| JP | 2011504495 A | 2/2011 |
| KR | 20090103227 A | 10/2009 |
| WO | 2007070164 A1 | 6/2007 |
| WO | 2012079504 A1 | 6/2012 |
| WO | 2012139424 A1 | 10/2012 |

(Continued)

OTHER PUBLICATIONS

Aitipamula et al. "Polymorphism: Fundamentals and Applications," Supramolecular Chemistry: From Molecules to Nanomaterials, (2012), 1-18.

Bassetti et al., "Development of Novel Antibacterial Drugs to Combat Multiple Resistant Organisms," Langenbecks Arch. Surg., (2015), 400: 153-165.

Extended European Search Report for EP Application No. 22160275. 8-1109; dated Jun. 28, 2022; 85 pages.

Hazra et al., "Tebipenem, a New Carbapenem Antibiotic, Is a Slow Substrate That Inhibits the β-Lactamase from *Mycobacterium tuberculosis*," Biochemistry, (2014), vol. 53, (No. 22), 3671-3678.

Hikida et al., "In Vitro Antibacterial Activity of LJC 11,036, an Active Metabolite of L-084, a New Oral Carbapenem Antibiotic With Potent Antipneumococcal Activity," Antimicrobial Agents and Chemotherapy, (1999), vol. 43, (No. 8), 2010-2016.

(Continued)

*Primary Examiner* — Susan T Tran
(74) *Attorney, Agent, or Firm* — CANTOR COLBURN LLP

(57) ABSTRACT

The disclosure provides a tebipenem pivoxil HBr formulation in the form of a tablet core comprising at least 70% (w/w) tebipenem pivoxil HBr, and in certain embodiment more than 80% (w/w) tebipenem pivoxil HBr. The disclosure provides a tebipenem pivoxil HBr tablet core comprising at least 70% w/w tebipenem pivoxil HBr, 5-25% w/w of a diluent, 0.5 to 5% w/w of a glidant, 0.5 to 5% w/w of a lubricant, and optionally 0.5 to 5% w/w of disintegrant. The disclosure provides methods of treating a patient who has a bacterial infection such as complicated urinary tract infection (cUTI), acute and chronic pyelonephritis, an upper or lower respiratory infection, or bacteremia by administering a formulation of the disclosure to the patient.

25 Claims, 5 Drawing Sheets

(56) References Cited

FOREIGN PATENT DOCUMENTS

| WO | WO-2018112372 A1 | * | 6/2018 | ............ | A61K 31/427 |
| WO | WO-2018145089 A1 | * | 8/2018 | ............ | A61K 31/431 |

OTHER PUBLICATIONS

International Preliminary Report on Patentability and Written Opinion of International Application No. PCT/US2017/066729; International Filing Date—Dec. 15, 2017; dated Jun. 18, 2019, 9 pages.

International Search Report; International Application No. PCT/US2017/066729; International Filing Date—Dec. 15, 2017; dated Apr. 24, 2018; 6 pages.

International Search Report; International Application No. PCT/US2021/059178; International Filing Date—Nov. 12, 2021; dated Apr. 22, 2022; 5 pages.

Muratani et al., "Antimicrobial Activity of Tebipenem Against Various Clinical Isolates from Various Specimen, Mainly Urinary Tract," The Japanese Journal of Antibiotics; (2009), vol. 62, (No. 2), 116-126.

Nakashima et al., "Effect of Probenecid or Diet on Tebipenem Pivoxil Tablets Pharmacokinetics in Healthy Male Volunteers," Hamamatsu Institute of Clinical Pharmacology & Therapeutics, (2009), vol. 57, (No. S-1), 103-108.

Nakashima et al., "Pharmacokinetics and Safety of Oral Carbapenem Antibiotic Tebipenem Pivoxil Tablets in Healthy Male Volunteers," Japanese Journal of Chemotherapy, (2009), vol. 57, (No. Suppl. 1), 82-89.

Tang et al., "Crystal Structure of Tebipenem Pivoxil," Crystallographic Communications, Acta Crystallographic Section E, (2018), E74, 1215-1217.

Written Opinion of the International Searching Authority for International Application No. PCT/US2021/059178; International Filing Date—Nov. 12, 2021; dated Apr. 22, 2022; 8 pages.

Written Opinion; International Application No. PCT/US2017/066729; International Filing Date—Dec. 15, 2017; dated Apr. 24, 2018; 9 pages.

Jain et al, "Tebipenem, the First Oral Carbapenem Antibiotic," Expert Review of Anti-Infective Therapy, (2018), 1-11.

* cited by examiner

HIGH DOSAGE TEBIPENEM PIVOXIL TABLET FORMULATION

CROSS REFERENCE TO RELATED APPLICATION

This application claims priority of U.S. Provisional Appl. No. 63/112,434 filed Nov. 11, 2020, which is hereby incorporated by reference in its entirety.

BACKGROUND

Tebipenem pivoxil is an orally administered pivaloyloxymethyl prodrug of tebipenem, an antibiotic from the carbapenem subgroup of β-lactam antibiotics.

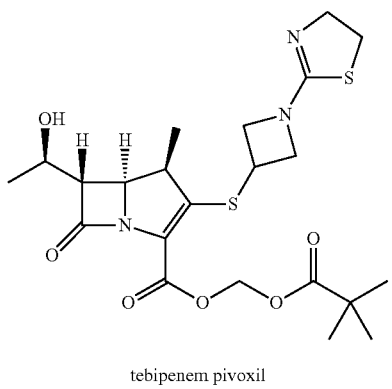 [SMILES: C[C@@H](O)[C@H]1C(=O)N2C(C(=O)OCOC(=O)C(C)(C)C)=C(SC3CN(C4=NCCS4)C3)[C@H](C)[C@H]12]

tebipenem pivoxil

Tebipenem pivoxil has been developed to treat severe bacterial infections that have acquired antibiotic resistance to commonly used anti-infective medicines. Following oral administration, the ester and acetal bonds of the prodrug are cleaved to release active tebipenem. Tebipenem Pivoxil may be administered as a free base but is preferably administered as a pharmaceutically acceptable salt, such as a hydrobromide salt (CAS Reg. No. 1381788-20-0). Clinical investigations have shown that 600 mg doses of tebipenem pivoxil (697.8 mg of the HBr salt), administered two or three times daily, are needed to treat certain infections in adult human patients, such as complicated urinary tract infections (cUTI) or pyelonephritis. Current dosage forms contain no more than 60% tebipenem pivoxil HBr, resulting in large dosage forms that are difficult for some patients to swallow. Thus, there is a need for tebipenem pivoxil dosage forms which contain a higher weight percent of drug and have an overall smaller size.

This disclosure provides dosage forms that meet this need and have additional advantages which are described in the disclosure.

SUMMARY

This disclosure provides tebipenem pivoxil HBr dosage forms containing a high weight percent of tebipenem pivoxil. In an embodiment the disclosure provides a tebipenem pivoxil tablet core comprising at least 65%, at least 70%, at least 75% and in certain embodiments at least 73% tebipenem pivoxil (w/w). In an embodiment the disclosure provides a tebipenem pivoxil HBr tablet core comprising at least 70%, at least 71%, at least 72%, at least 73%, at least 74%, at least 75%, at least 76%, at least 77%, at least 77.5%, at least 80%, at least 82%, at least 85%, or at least 87% (w/w) tebipenem pivoxil HBr. Certain embodiments comprise at least 77% tebipenem pivoxil HBr (w/w). The tebipenem pivoxil HBr tablet core can comprise at least 70% (w/w) tebipenem pivoxil HBr, 15-25% w/w of a diluent, 0.5 to 5% w/w of disintegrant, 0.5 to 5% w/w of a glidant, and 0.5 to 5% w/w of a lubricant. For example, a tebipenem pivoxil HBr tablet core can comprise at least 70% tebipenem pivoxil HBr, 15-25% w/w of microcrystalline cellulose, e.g. grades PH101, PH102, PH103, PH105, PH112, PH113, PH200, and PH301 and combinations of the foregoing, preferably PH101; 0.5 to 5% w/w of crospovidone, e.g. POLYPLASDONE XL-10; 0.5 to 2.0% w/w of colloidal silicon dioxide, grade 200; and 0.5 to 5% w/w of magnesium stearate. The disclosure further includes a process for preparing the described tebipenem pivoxil dosage forms.

The disclosure also includes methods of treating a bacterial infection in a patient, comprising administering a tebipenem pivoxil HBr tablet core or tablet of the disclosure to the patient. In certain embodiments the tablet core is coated with a functional or non-functional coating. In certain embodiments the coating is a non-functional coating, such as a non-functional film coating, that does not significantly affect the immediate release characteristics of the tablet core. The patient may be a human patient or a mammalian patient, such as a livestock animal or companion animal. For example, the bacterial infection can be a urinary tract infection. The bacterial infection can also be a Gram negative bacterial infection. The bacterial infection can also be an *E. coli* infection, a *Klebsiella pneumoniae* infection, an *Acinetobacter baumannii* infection, a *Pseudomonas aeruginosa*, a *Neisseria gonorrhoeae* infection, or a *Yersinia pestis* infection.

DETAILED DESCRIPTION OF THE INVENTION

Terminology

Figure 1:
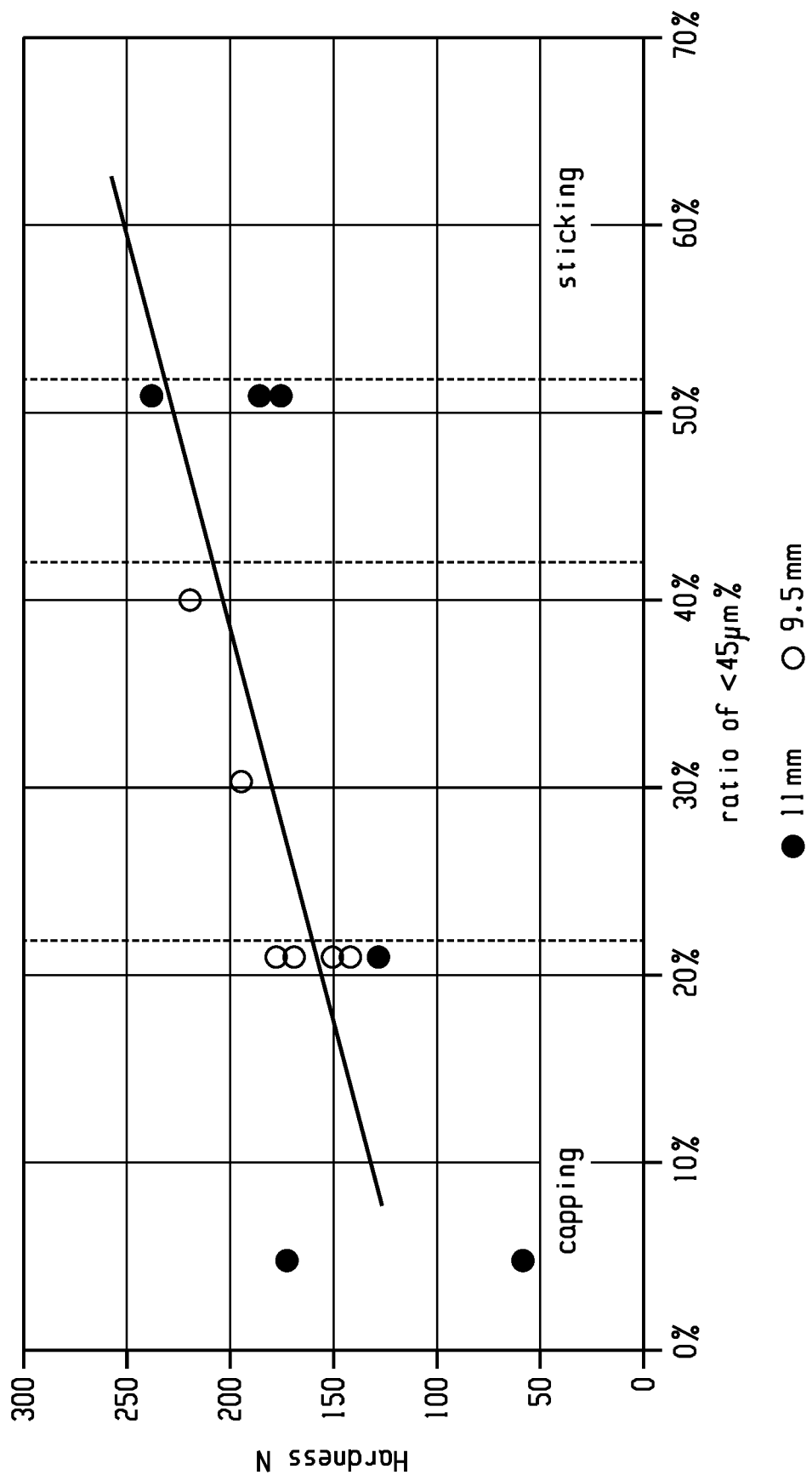
FIG. 1. Correlation of the ratio of particles smaller than 45 μm and the hardness of the core tablet produced.

Prior to describing the disclosure in detail, the following terms may be helpful. Unless otherwise specified all terms carry their ordinary meaning, accepted in the art of pharmaceutical formulations or methods of treating bacterial infections in patients.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or language indicating an example (e.g., "such as"), is intended merely for illustration and does not pose a limitation on the scope of the invention unless otherwise claimed. No language in the specification should be construed as indicating any non-claimed element as essential to the practice of the invention.

The terms "a" and "an" do not denote a limitation of quantity, but rather denote the presence of at least one of the referenced items.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe are included in the value. Thus, compositions slightly outside the cited ranges are also encompassed by the scope of the present claims.

The terms "comprising," "including," and "containing" are non-limiting. Other non-recited elements may be present in embodiments claimed by these transitional phrases. Where "comprising," "containing," or "including" are used as transitional phrases other elements may be included and still form an embodiment within the scope of the claim. The open-ended transitional phrase "comprising" encompasses the intermediate transitional phrase "consisting essentially of" and the close-ended phrase "consisting of."

When a weight of tebipenem pivoxil that may be in a salt form is given the value refers to the amount of tebipenem pivoxil rather than the weight of tebipenem pivoxil salt. For example, 500 mg of tebipenem pivoxil, where the tebipenem pivoxil is a hydrobromide salt, indicates that 581.2 g of tebipenem pivoxil hydrobromide are present. Unless it is clear from the context that tebipenem pivoxil free base is intended or tebipenem pivoxil free base is explicitly specified the term "tebipenem pivoxil" includes tebipenem pivoxil free base and the pharmaceutically acceptable salts of tebipenem pivoxil, for example tebipenem pivoxil HBr. Tebipenem pivoxil HBr is a commercial embodiment and is included in all instances in which tebipenem pivoxil tablets, tablet cores, or formulations are discussed, unless the context clearly indicates otherwise.

"Providing" means giving, administering, selling, distributing, transferring (for profit or not), manufacturing, compounding, or dispensing.

"Treatment," as used herein includes providing the crystalline tebipenem pivoxil salt form and at least one additional active agent sufficient to: (a) reduce probability a disease or a symptom of a disease from occurring in a patient who is be predisposed to the disease but has not yet been diagnosed as having it (e.g. prevent bacterial infection in a patient traveling to an area where risk of exposure to bacterial infection is high); (b) inhibiting the disease, i.e. arresting its development; and (c) relieving the disease, i.e., causing regression of the disease. "Treating" and "treatment" also means providing a therapeutically effective amount of the crystalline tebipenem pivoxil salt form and at least one additional active agent to a patient having or susceptible to microbial infection, such as an antibiotic resistant bacterial infection or a Gram-negative bacterial infection.

A "therapeutically effective amount" of a pharmaceutical combination of this disclosure means an amount effective, when administered to a patient, to provide a therapeutic benefit such as an amelioration of symptoms, e.g., an amount effective to decrease the symptoms of a bacterial infection. For example, a patient infected with a bacterial infection may present abnormal levels of certain blood cells, especially leukocytes (white blood cells) for example, an increase in neutrophils and a decrease in lymphocytes. A therapeutically effect amount is thus an amount sufficient to provide a return of leukocyte levels to the normal range. A therapeutically effective amount is also an amount sufficient to prevent a significant increase or significantly reduce the detectable level of bacteria or bacterial antibodies in the patient's blood, serum, or tissues.

Pharmaceutical Formulations

The disclosure provides tebipenem pivoxil HBr tablet formulations in which tebipenem pivoxil comprises at least 61%, at least 62%, at least 63%, at least 64%, at least 65%, at least 66%, at least 67%, at least 68%, at least 69%, at least 70%, at least 71%, at least 72%, at least 73%, at least 74%, or at least 75%, (w/w) of the tablet core. The tablet is typically a tebipenem pivoxil HBr tablet, but unless otherwise specified the weight or weight percentage refers to tebipenem pivoxil. Tablet cores in which tebipenem pivoxil HBr comprises at least 69%, at least 70%, at least 71%, at least 72%, at least 73%, at least 74%, at least 75% at least 76%, at least 77%, at least 80%, at least 82%, or at least 85% (w/w) of the tablet core are also provided. The disclosure also provides tebipenem pivoxil HBr tablet formulations in which tebipenem pivoxil HBr comprises at least 70%, at least 75%, or at least 77% (w/w) of the tablet core. The high weight percent tebipenem pivoxil tablet cores, including tebipenem pivoxil HBr tablet cores, of the disclosed tablet formulations provide an advantage over previously reported tebipenem formulations. Because an effective daily oral dose of tebipenem pivoxil for an adult human patient is 1800 mg (600 mg TID), a high tebipenem pivoxil content tablet is needed to provide an easily swallowed and acceptable dosage form for the patient. The tablet dosage forms of this disclosure can contain tebipenem pivoxil in the form of its free base or as a pharmaceutically acceptable salt of tebipenem pivoxil, such as tebipenem pivoxil hydrobromide are particularly disclosed. The tebipenem pivoxil can be in the form of a tebipenem pivoxil hydrobromide crystalline form or tebipenem pivoxil hydrobromide amorphous form. The crystalline form may be a single polymorph, or a mixture of two or more polymorph forms, such as tebipenem pivoxil hydrobromide Form B or Form C or a mixture of any of the foregoing. In an embodiment the tebipenem pivoxil is present as tebipenem pivoxil hydrobromide crystalline form B.

A mixture of crystalline and amorphous tebipenem pivoxil HBr forms can be present (such as tebipenem pivoxil HBr Form B and/or Form C and amorphous tebipenem pivoxil HBr). Tebipenem pivoxil hydrobromide crystalline Form B has been described in U.S. application Ser. No. 16/483,989 filed Aug. 6, 2019, now U.S. Pat. No. 10,889,587, which is hereby incorporated by reference for its teachings regarding crystalline forms of tebipenem pivoxil. The tebipenem pivoxil hydrobromide crystalline form B, which has XRPD obtained from a Cu Kα source at any 5, 6, 7, 8, 9, 10, 11, 12 or more of the following values: 9.3, 9.5, 10.7, 12.6, 13.0, 14.0, 15.2, 15.7, 17.6, 18.7, 19.1, 20.0, 20.4, 20.8, 21.1, 21.9, 22.6, 23.5, 23.7, 24.9, 25.3, 25.5, 25.8, 26.1, 26.5, 26.8, 27.3, 27.6, 28.4, 28.8, 29.4, 29.7, or 29.9+/−0.2 degrees 2θ. The tebipenem pivoxil hydrobromide may also be in the form of crystalline Form C (also described in U.S. application Ser. No. 16/483,989), which has XRPD obtained from a Cu Kα source at any 5, 6, 7, 8, 9, 10, 11, 12 or more of the following values: 4.4, 8.7, 9.3, 12.1, 13.1, 14.2, 15.5, 16.3, 16.5, 17.1, 17.3, 17.6, 18.5, 19.3, 19.7, 20.8, 21, 21.3, 21.7, 22.2, 22.6, 22.8, 23.5, 24.0, 24.4, 25.2, 25.5, 26.4, 26.7, 27.4, 28.2, 28.8, 29, 29.5, 29.7, 30, and 30.5.

In an embodiment the tebipenem pivoxil is present as tebipenem pivoxil mesylate (methane sulfonate) crystalline form B, which has XRPD obtained from a Cu Kα source at any 5, 6, 7, 8, 9, 10, 11, 12 or more of the following values: 9.1, 9.6, 10.9, 12.6, 13.9, 14.6, 15.4, 17.2, 17.5, 18.2, 18.4, 18.7, 19.4, 19.6, 19.8, 20.4, 20.6, 21.5, 21.9, 22.2, 22.9, 23.6, 24.5, 25.3, 25.6, 26.4, 26.9, 27.1, 27.5, 27.8, 28.0, 28.6, 29.4, or 29.8.

The disclosure includes a process of preparing a tebipenem pivoxil tablet core in which the tebipenem pivoxil, which may be in the form of tebipenem pivoxil HBr, is blended with a disintegrant or diluent. In certain embodiments tebipenem pivoxil or tebipenem pivoxil HBr in which 20-40% of particles pass through a JP #300 mesh (sieve opening 45 μm). Particle size may be adjusted by use of a Comil or by use of a use of drug substance known to have 20-40% of drug particles able to pass through a JP #300 mesh.

Other pharmaceutically acceptable salt forms of tebipenem pivoxil that may be used in the tablet formulations of this disclosure include tebipenem pivoxil hydrogen chloride, methane sulfonate, ethane sulfonate, ketoglutarate, or maleate.

The disclosure includes a tebipenem pivoxil HBr tablet core comprising an amount of tebipenem pivoxil HBr listed above, for example comprising at least 65% w/w, at least 70% % w/w, at least 73% w/w, or at least 75% w/w, and also comprising 15-25% w/w of a diluent/binder, 0.5 to 5% w/w of disintegrant, 0.5 to 5% w/w of a glidant, and 0.5 to 5% w/w of a lubricant. The disclosure includes a tebipenem HBr tablet core comprising an amount of tebipenem pivoxil HBr listed above, for example comprising at least 65% w/w, 70% % w/w, at least 73% w/w, or at least 75% w/w, and also comprising 15-25% w/w of microcrystalline cellulose, e.g. grade PH101; 0.5 to 5% w/w of crospovidone XL-10; 0.5 to 2.0% w/w of colloidal silicon dioxide, e.g. grade 200; and 0.5 to 5% w/w of magnesium stearate.

The tablet core contains a binder or diluent. Suitable diluents include soluble and insoluble diluents. Insoluble diluents include starch, such as maize starch, potato starch, rice starch, wheat starch, and pregelatinized starches. Insoluble diluents include celluloses such as crystalline celluloses, microcrystalline celluloses, and powdered celluloses. Examples include AVICEL PH-101 (Millipore-Sigma, SUN-A TEC), PH-102 (CAS Reg. No. 9004-34-6) or AVI-CEL-301 both having a 50 μm particle size, AVICEL PH-102 (100 μm particle size), AVICEL PH-302, and microcrystalline cellulose 112. Other useful insoluble diluents include, but are not limited to, calcium carbonate, magnesium carbonate, dibasic calcium phosphate, directly compressible grades of dibasic calcium phosphate (EMCOMPRESS), tribasic calcium phosphate, and any combinations thereof. Insoluble diluents also include silicified MCC (PROSOLVE V from JRS Pharma, Germany), a multifunctional ingredient containing 98% microcrystalline cellulose and 2% colloidal silica, where silica is distributed over the surface of particles.

Soluble binder/diluents include microcrystalline cellulose, silicified microcrystalline cellulose, cellulose, calcium phosphate, anhydrous calcium phosphate, calcium hydrogen phosphate dihydrate, sugar alcohols such as mannitol, lactose, lactose monohydrate, anhydrous lactose, starch, pregelatinized starch, talc, sorbitol, xylitol and the like. Suitable grades of lactose include but are not limited to lactose monohydrate, lactose DT, lactose anhydrous, spray dried lactose such as FLOWLAC 90 or FLOWLAC 100 (Meggle Pharma, Wasserburg, Germany), milled lactose such as PHARMATOSE 100M or PHARMATOSE 200M (DFE Pharma, Goch, Germany). Suitable microcrystalline celluloses include PROSOLV® SMMC 50 (JRS Pharma GmbH & Co, Rosenberg, Germany), a mixture of microcrystalline cellulose and colloidal silicon dioxide having an average particle size of 65 μm and a bulk density of 0.25-0.37 g/mL, and PROSOLV® SMMC 90, a mixture of microcrystalline cellulose and colloidal silicon dioxide having an average particle size of 125 μm and a bulk density of 0.25-0.37 g/mL.

The disclosure includes tebipenem pivoxil and tebipenem pivoxil HBr tablet cores in which the binder/diluent is microcrystalline cellulose, for example grade PH 101.

The tebipenem pivoxil or tebipenem pivoxil HBr tablet cores contain a disintegrant. For example, the disintegrant may be croscarmellose sodium, crospovidone (also called copovidone), sodium starch glycolate, or any combination of any two or more of the foregoing. The disintegrant may be present in the tablet core or coated tablet in an amount (% w/w) from 0.1% to 10% (w/w) or from 0.5% to 5% (w/w), or from 0.5 to 2% (w/w) or about 1% (w/w). In some embodiments PVPP XL-10, a type of crospovidone, is the disintegrant. PVPP XL-10 is a crosslinked polyvinylpyrrolidone having an average particle size of 30 μm. Other suitable disintegrants include croscarmellose sodium, pregelatinized starch, sodium starch glycolate, mannitol, maize starch, potato starch, alginic acid, and wheat starch.

The disclosure includes tebipenem pivoxil and tebipenem pivoxil HBr tablet cores in which the disintegrant is crospovidone (cross linked polyvinyl N-pyrrolidone). In certain embodiments the disintegrant is crospovidone of a grade having a D50 (median diameter particle size) 25 to 40 microns. In certain embodiments the disintegrant is crospovidone crospovidone XL-10 or Ultra-10.

The disclosure includes tebipenem pivoxil and tebipenem pivoxil HBr tablet cores comprising a glidant. The glidant may comprise 0.5% to 5% w/w of the tablet core. A glidant is a substance that improves the flowability of a powder, reduces interparticle friction within a powder, and reduces the cohesion of powder particles. Glidants act, for example, by reducing interparticular friction and decreasing surface charge. Reduction in angle of repose is an indication of a glidant's efficacy and enhanced powder flowability. Suitable glidants include talc, such as hydrous magnesium calcium silicate, hydrous magnesium silicate, Altalc, and E553b, and silicon dioxide, including colloidal silicon dioxide.

The disclosure includes tebipenem pivoxil tablet cores containing 0.5-2.0% w/w of a glidant, wherein the glidant is silicon dioxide. The disclosure includes tebipenem pivoxil and tebipenem pivoxil HBr tablet cores containing 0.5-2.0% w/w of a glidant, wherein the glidant is colloidal silicon dioxide, e.g., grade 200.

The disclosure includes tebipenem pivoxil and tebipenem pivoxil HBr tablet cores comprising a lubricant. Lubricants are added to reduce friction during tablet formation, including tablet compression. A lubricant can prevent sticking of the tablet to punch faces or tableting presses. A lubricant for use in the tablet cores of this disclosure can be water soluble or water insoluble, though is water insoluble in the exemplified embodiments. Water soluble lubricants include boric acid, sodium benzoate, sodium oleate, sodium acetate, sodium lauryl sulphate, and magnesium lauryl sulphate. Water insoluble lubricants include magnesium stearate, calcium stearate, waxes, glyceryl behenate, or liquid paraffin.

The disclosure includes tebipenem pivoxil HBr tablet cores comprising 0.5-2.0% w/w of a lubricant. In certain embodiments the lubricant is magnesium stearate.

Preparation of Reduced Size Tebipenem Pivoxil HBr Tablets

Preliminary studies (not included) indicated it was possible to reduce the amount of microcrystalline cellulose to 13%-30% of the coated tablet weight and obtain a formulation that could be compressed properly into an uncoated tablet formulation. These preliminary uncoated tablet formulations were not optimized for size or other tablet properties such as capping and sticking.

In Formulations 1-4 (Example 2), the amount of crospovidone was reduced or crospovidone was eliminated in effort to extend the disintegration time. Formulations 1-3 showed capping during compression. Microcrystalline cellulose, 26.996 g (AVICEL® PH102) was added to 300 g of the Formulation 1 blend and compressed after blending. These tablets, labeled Formula 1, also exhibit capping. Formulation 4 mixture was compressed without capping or other defects; however, the core tablet hardness was low. It may be possible to avoid table capping by altering compression parameters or controlling drug substance parameters. Granulation of drug substances can be used to increase compressibility and reduce tablet capping.

Crospovidone was added back to the formulation, in attempt to produce a formulation without capping. Capping occurred as the compression pressure was increased to 20 kN. Capping was avoided by switching from an φ11 mm punch/die with emboss to a φ9.5 mm punch/die without emboss and setting the pre-compression force to 300 kg. Compression of this formulation (details not shown) without capping was achieved even as the compression pressure was increased to 20 kN.

Formulations 5-7 used microcrystalline cellulose having smaller particle size (Microcrystalline cellulose (CEOLUS® PH101)) or used a commercially available pre-mixture of microcrystalline cellulose and silicon dioxide (e.g., PROSOLV® SMCC 50 and PROSOLV® SMCC 90, both mixtures of silicified microcrystalline cellulose and colloidal silicon dioxide). Formulation 5 using PROSOLV® SMCC 50 and Formulation 6 using Microcrystalline cellulose (AVICEL PH101) gave the proper compression. However, capping occurred in Formulation 7, which used the PROSOLV® SMCC 90.

Formulation 8/9, 10, and 11 adjusted amount of drug particles which pass through a JP #300 mesh (sieve opening 45 μm) to 20-40% by using either Comil-ed drug substance or a lot of drug substance known to have 20-40% of drug particles in this size range. Crospovidone was omitted from Formulation 10 to extend disintegration time.

Figure 3:
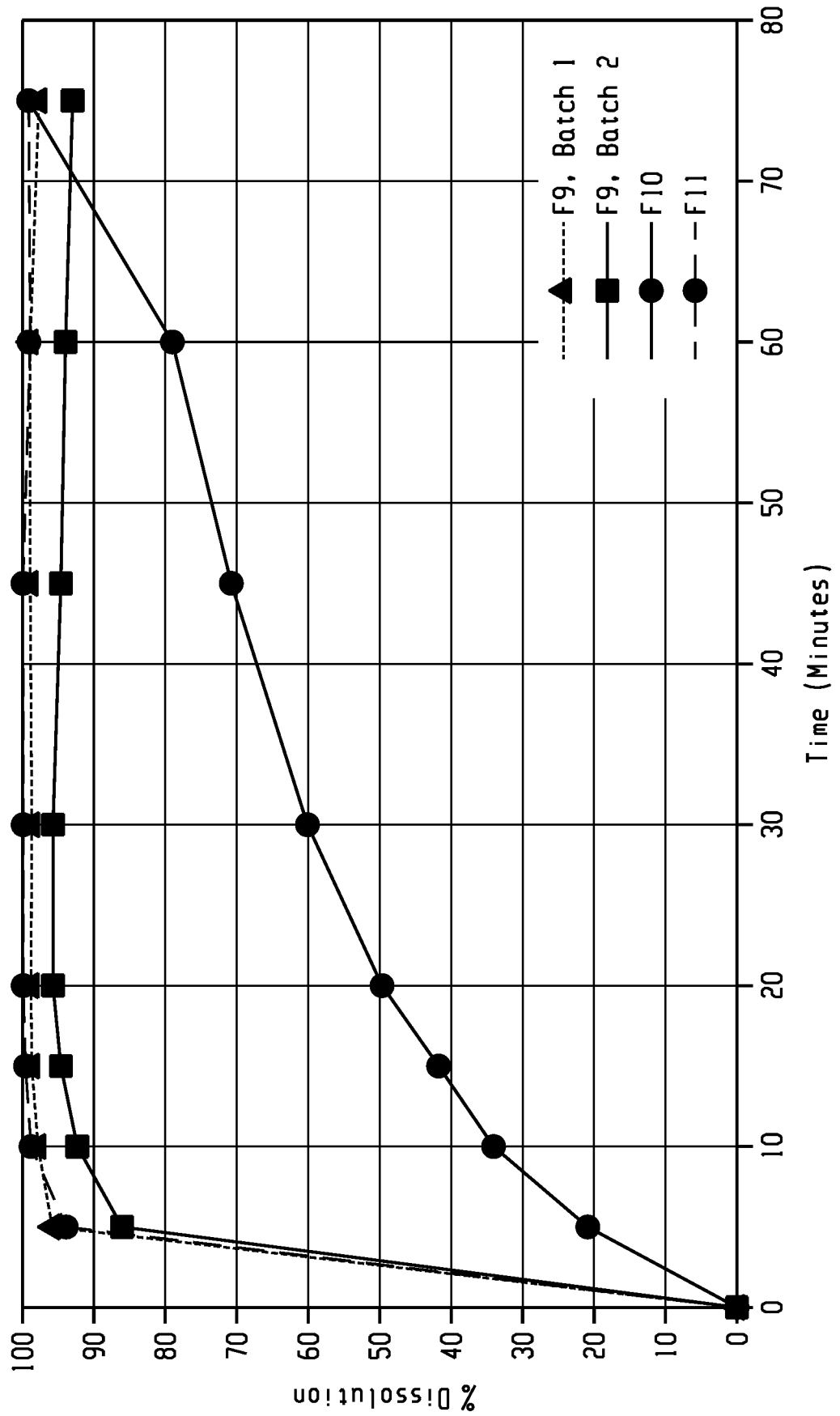
FIG. 3. Dissolution profiles (% Dissolution vs. Time) for Formulation 9-11.

Formulations 9 and 10 contain 30-40% drug substance particles from a manufacturing lot that pass the JP #330 mesh (sieve opening 45 μm). The formulations provide the proper compression. Formulations 8 and 11 contain Comiled drug substance particles, 20% of these particles pass through a JP #330 mesh (sieve opening 45 μm). These formulations showed capping at high compression pressure. Formulation 10 exhibited proper compression, and a disintegration time that was extended to about 15 minutes. FIG. 3 shows the dissolution profiles of Formulations 9-11. Two batches of Formulation 9 of different batch sizes were tested.

Capping and sticking were two tablet defects encountered while formulating tebipenem pivoxil HBr tablet cores. Tablet composition was found to be a factor in achieving a tablet core that compressed without capping and sticking. Physical properties of the drug substance were also a factor. Process parameters including compression force, precompression force, compression depth (die depth), and turret speed (dwell time) also affect tablet compression.

Figure 2:
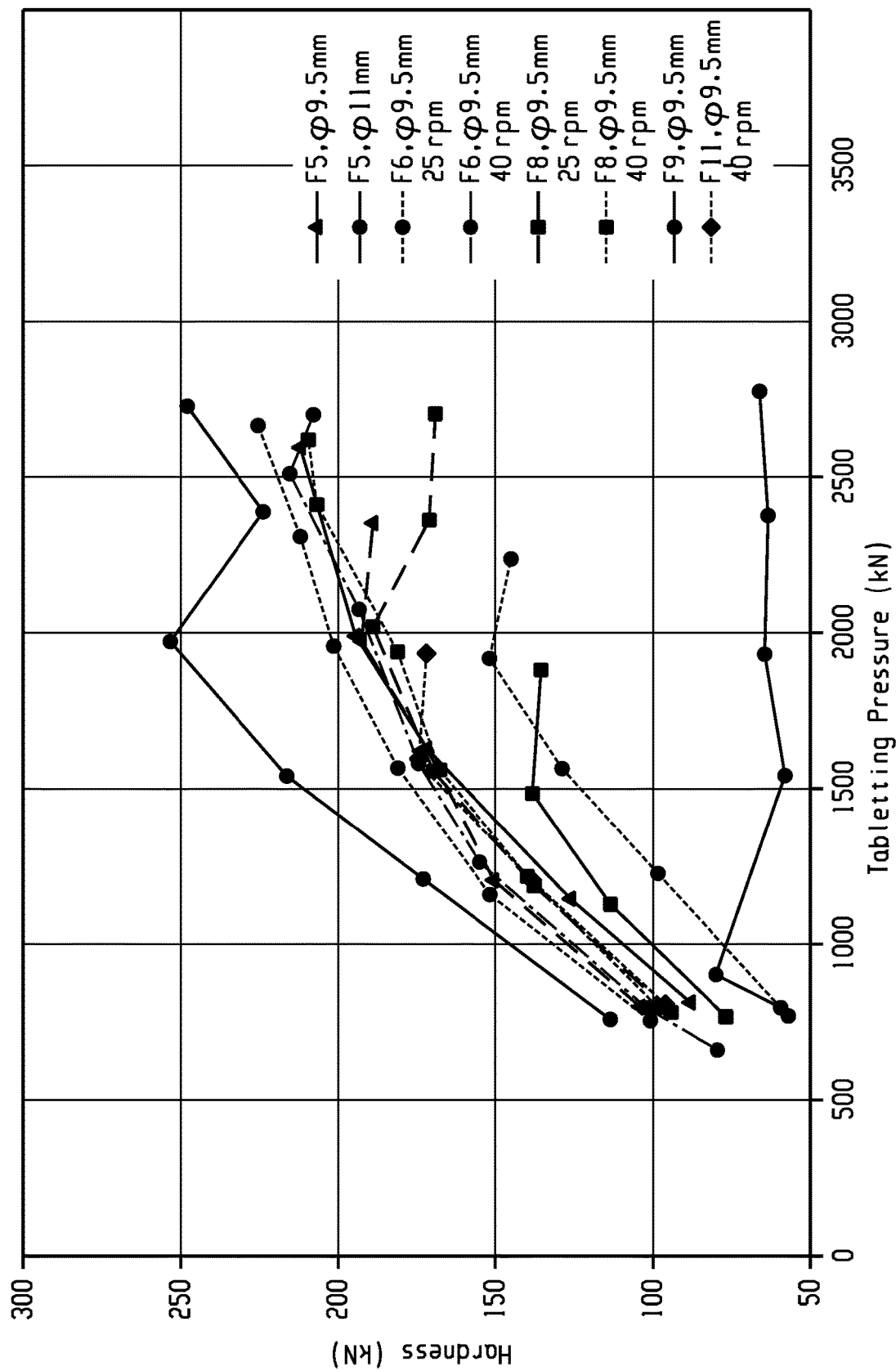
FIG. 2. Correlation between main compression pressure and core tablet hardness for Formulations 4-11.

Generally, for tablet formulation that provides proper compression, tablet core hardness increases with main compression force, until the hardness plateaus at a certain high compression pressure. The correlation of main compression pressure and core tablet hardness is shown in FIG. 2. Dwell time also affects tablet core hardness and is not accounted for in FIG. 2.

API Particle Size

We have determined that controlling drug substance particle size within a narrow range avoids both capping and sticking as the high dose tablet cores are compressed. Accordingly, the disclosure provides tebipenem pivoxil tablet formulations, including tebipenem pivoxil HBr tablet formulations, in which 20%-50%, more preferably 18-42%, and more preferably 20-40%, of tebipenem pivoxil, e.g. tebipenem pivoxil HBr, used in the tablet core blend has a particle size less than 45 μm. Tebipenem pivoxil particles, e.g. tebipenem pivoxil HBr particles, used in the tablet core blend can also have a D50 of less than 100 μm, less than 90 μm, or less than 80 μm, or between 60 and 90 μm, or between 70 and 80 μm. The disclosure provides a process of making tebipenem pivoxil tablet cores that includes blending tebipenem pivoxil particles meeting any of these parameters with a disintegrant, such as crospovidone, or a diluent, such as microcrystalline cellulose.

This disclosure provides tebipenem pivoxil tablet cores, e.g., tebipenem pivoxil HBr tablet cores, in which the particle size of the tebipenem pivoxil has been controlled to within a narrow range, for example so that 20-40% tebipenem pivoxil particles pass through a JP #330 mesh (sieve opening 45 μm). In certain instances, tebipenem pivoxil or tebipenem pivoxil HBr, drug substance may meet these criteria immediately following synthesis. Often, it will be necessary to control the particle size of tebipenem pivoxil following synthesis. A QUADRO COMIL machine—a wet/dry conical mesh screen milling machine, for example equipped with a $\overline{\varphi}$ 0.610 mm, φ0.457 mm, or φ0.279 mm mesh and using a round impeller and rotary speed of 2500 rpm, may be used to control particle size. A pharmaceutical ingredient that has been processed by such a machine is "Comil-ed." Repeated sieving of tebipenem pivoxil HBr drug particles under the above Comil conditions did not further reduce the tebipenem pivoxil HBr particle size. Other options for controlling drug substance particle size include mechanical sieve mills, micronization techniques such as mechanical interaction or gas micronization techniques, and electrospraying.

Whether newly synthesized or "comil-ed" batch of tebipenem pivoxil meets the particle size criteria can be determined by sieving the drug substance through a mesh having a 45 μm sieve opening and weighing the fraction that passes through the sieve. As tebipenem pivoxil particle size is important for achieving high weight percentage tebipenem pivoxil tablet cores, e.g. high weight percentage tebipenem pivoxil HBr tablet cores, with adequate compaction properties the particle size distribution (by sieve method) for two tebipenem pivoxil HBr batches that provided adequate compaction properties, including compressibility of drug substance are given in Table 1.

TABLE 1

| Sample | 300 um< | 150 um< | 106 um< | 75 um< | 45 um< | <45 um |
|---|---|---|---|---|---|---|
| Lot 1, Comil-ed | 0% | 1% | 16% | 27% | 35% | 21% |
| Lot 2 | 0% | 2% | 6% | 6% | 46% | 40% |

The disclosure provides tablet cores containing tebipenem pivoxil HBr particles having a D90 of less than 160 μm, less than 150 μm, between 120 μm and 160 μm, or between 130 and 150 μm, and/or having a D50 of less than 100 μm, less than 90 μm, or less than 80 μm, or less than 70 μm. The disclosure also provides tebipenem pivoxil HBr tablet cores containing tebipenem pivoxil HBr particles between 40 and 90 μm, or between 40 and 70 μm. The disclosure provides tablet cores in which 20%-50%, and more preferably 20-40%, of tebipenem pivoxil HBr has a particle size less than 45 μm.

The disclosure provides a process for preparing tebipenem pivoxil HBr tablet cores having a high percentage (wt %, also w/w) tebipenem pivoxil HBr comprising blending tebipenem pivoxil HBr particles with a disintegrant, the tebipenem pivoxil particles having a D90 of less than 160 μm, less than 150 μm, between 120 μm and 160 μm, or between 130 and 150 μm, and/or having a D50 of less than 100 μm, less than 90 μm, less than 80 μm or less than 70 μm, or between 40 and 90 μm, or between 40 and 70 μm.

The particle size distribution of the tebipenem pivoxil HBr can be determined, for example, by a laser diffraction particle sizer, such as a Sheishin LMS-2000e, or by sieve cut analysis.

Process

The disclosure includes a process for making tebipenem pivoxil (e.g. tebipenem pivoxil HBr) tablet cores containing a high weight percent of tebipenem pivoxil, or salt thereof such as tebipenem pivoxil HBr.

The disclosure provides a process of making tebipenem pivoxil tablet cores that includes blending tebipenem pivoxil with a disintegrant, such as crospovidone, and also blending the diluent, such as microcrystalline cellulose, with a glidant, such as silicon dioxide. The blend of tebipenem pivoxil and disintegrant is blended with the mixture of diluent, such as microcrystalline cellulose. Alternatively, a commercially available silicified microcrystalline cellulose can be used.

Depending on the physical properties of the drug substance, the grade of silicified microcrystalline cellulose, and the type and amount of disintegrant used, the blend times and blend speed will vary. Selection of optimum blend time and speed can be made by one of ordinary skill in the art. For example, the blend time may be 10 minutes to 4 hours, 20 minutes to 2 hours, 30 minutes to 2 hours, or 30 minutes to 60 minutes. The blend speed may be adjusted, for example 5 rpm to 20 rpm, 5 rpm to 15 rpm, 5 rpm to 10 rpm, or about 8 rpm. The contents of the bin blender are blended, for example for 30-60 minutes at 8.0 rpm.

The process includes adding lubricant, such as magnesium stearate, to the mixture of drug substances, diluent, and disintegrant. Magnesium stearate can be added to a mixture of drug substance, disintegrant, and diluent in the bin blender. The lubricant, e.g., magnesium stearate, can be pre-screened to ensure uniform size or otherwise treated prior to being added to the bin blender. The lubricant, e.g., magnesium stearate, is blended with the contents of the bin blender, for example for 1 minute to 1 hour, 1 minute to 30 minutes, 2 minutes to 15 minutes, or 3-10 minutes, at a speed 5 rpm to 20 rpm, 5 rpm to 15 rpm, 5 rpm to 10 rpm, or about 8 rpm.

The magnesium stearate containing blend is compressed using a rotary press to form the tablet cores. Cores can be coated with a functional or non-functional, such as Opadry II, in a coating pan. Cores are typically coated for a target of 3% w/w weight gain.

Coatings

The finished tebipenem pivoxil HBr dosage form may include a coating. The coating may be a single layer functional or non-functional coating on the tablet core or may be a non-functional coating layered a functional or non-functional membrane on a tablet core.

The tebipenem pivoxil HBr table core may be coated with an immediate release coating. Suitable coating materials include coatings comprised of cellulosic polymers, such as HPMC (hydroxypropyl methyl cellulose or hypromellose) as water soluble film coating agent, such as grades 1828, 2208, 2906, or 2910, also known as hypromellose and hypromellose USP also known as hydroxypropyl methylcellulose (HPMC). Other cellulosic polymer coatings include hydroxypropyl cellulose (HPC), hydroxyethyl cellulose (HEC), methylcellulose (MC), and sodium carboxymethyl cellulose (NaCMC). Coatings can also be vinyl derivatives, such as polyvinylpyrrolidone (PVP), polyvinyl pyrrolidone-polyvinyl acetate copolymers, polyvinyl alcohol (PVA), polyvinyl alcohol-polyethylene glycol copolymers. The coating can be an acrylic coating, such as an EUDRAGIT. The coating can comprise a glycol, such as a polyethylene glycol product (PEG) or PHARMACOAT (ShinEtsu Chemical-Co., Ltd.). PHARMACOAT 603 is a hypromellosegrade having substitution type 2910 and a labeled viscosity of 3 mPa-s that is suitable for use as a film coating. The OPADRY tradename is used for a variety of pharmaceutical coatings, and includes immediate release coatings, comprised primarily of HPMC (hydroxypropyl methyl cellulose or hypromellose) or PVA (polyvinyl alcohol) and PEG (polyethylene glycol). PEG may be used as a plasticizer in OPADRY coatings. EUDRAGITs, such as EUDRAGIT L 100-55, are another suitable class of coatings. EUDRAGITs are copolymers derived from esters of acrylic and methacrylic acid, with additional functional groups in some cases.

The coating can be an aqueous film coating, such as a PVA based coating, for example Colorcon's OPADRY II, a PVA based film coating. The coating may include additional excipients such as film formers, printing inks, buffering agents, pH adjusters, preservatives, dyes, and flavors. In some instances, a single material will include any two or more of any of the foregoing excipients.

The thickness of the 300 mg tebipenem pivoxil tablet may be from 5.00 to 8.00 millimeters (mm), or from 6.00 to 7.00 mm, or from 6.50 to 7.00 mm, or from 6.75 to 7.00 mm. An amount of the coating of the tablet is from 1 to 5 weight percent of the total weight of the tablet, for example, from 2 to 3 weight percent of the total weight of the tablet.

Embodiments may be combined only so long as a stable solid formulation or its core results. "A combination of any of the foregoing" only includes combinations that result in a stable tablet or tablet core.

Final, coated or uncoated tablets may also be debossed. For example, coated tablets may be debossed with letters denoting tebipenem, e.g. "TBM." or the dosage size, e.g. 300 or 600 mg.

Methods of Treatment

The disclosure includes a method of treating a bacterial infection in a patient by administering a tebipenem pivoxil HBr dosage form of the disclosure to a patient at risk for a bacterial infection or suffering from a bacterial infection. The disclosure includes methods of treating acute and chronic bacterial infections.

Treatment of human patients is particularly contemplated. However, treatment of non-human patients, such as livestock or companion animals, is within the scope of the disclosure.

In some embodiments, the bacterial infection or antibiotic-tolerant or antibiotic-resistant infection is caused by a Gram-negative bacterium. In some embodiments the bacterial infection is caused by a Gram-positive bacterium.

In some embodiments, the bacterial infection is an extended-spectrum beta-lactames (ESBL)-producing bacterial infection, AmpC beta-lactamase producing bacterial infection, a levofloxacin nonsuceptible bacterial infection, a TMP-SMX-resistant *E. coli* infection, a fluoroquinolone-resistant or fluoroquinolone non-susceptible bacterial infection, an Enterobacterales resistance phenotype bacterial infection, or a trimethoprim-sulfamethoxazole-resistant (TMP-SMX) bacterial infection. Methods of treatment include determining that a patient is infected with extended-spectrum beta-lactamase (ESBL)-producing bacteria, AmpC beta-lactamase producing bacteria, a levofloxacin nonsuceptible bacteria, a TMP-SMX-resistant bacterial infection, or a fluoroquinolone-resistant bacteria, or any combination of the foregoing and treating the patient with tebipenem pivoxil HBr. Such bacterial infections can be UTIs including cUTIs. Methods of treatment include determining a patient, such as a patient having an UTI, is infected with an antibiotic resistant *E. coli*, such as extended-spectrum beta-lactamase (ESBL)-producing *E. coli*, a levofloxacin resistant *E. coli*, a TMP-SMX-resistant *E. coli*, or a fluoroquinolone-resistant *E. coli*, or any combination of the foregoing and treating the patient with tebipenem pivoxil HBr. Methods of treatment include determining whether a patient is infected with a ESBL *E. coli* carrying blaCTX-M, blaSHV-12, blaCMY, blaDHA, or blaKPC-2 and treating the patient tebipenem pivoxil HBr.

Tebipenem pivoxil is effective against bacterial pathogens overexpressing AmpC. An embodiment comprises determining whether a patient has an infection with a bacterial pathogen overexpressing AmpC and administering an effective amount of tebipenem pivoxil in a formulation of this disclosure to the patient.

In some embodiments, the infection is a mycobacterial infection. The mycobacterial infection can be a non-tuberculous mycobacterial (NTM) infection such as a *Mycobacterium ulcerans* infection, leprosy (Hansen's disease), a *Mycobacterium abscessus* infection, *Mycobacterium parascrofulaceum* infection, or a *Mycobacterium kansasii* infection.

The tebipenem pivoxil oral dosage form of this disclosure may be administered alone, so that tebipenem pivoxil is the only active agent administered to the patient or the dosage form may be administered in combination with one or more additional active agents. Combination administration includes concurrent or sequential administration of active agents.

In an embodiment of any of the methods of this disclosure, the microbial infection is the result of a pathogenic bacterial infection. Examples of pathogenic bacteria include, without limitation, bacteria within the genera *Aerobacter, Aeromonas, Acinetobacter, Agrobacterium, Bacillus, Bacteroides, Bartonella, Bordetella, Brucella, Burkholderia, Calymmatobacterium, Campylobacter, Citrobacter, Clostridium, Corynebacterium, Enterobacter, Enterococcus, Escherichia, Francisella, Fusobacterium, Haemophilus, Hafnia, Helicobacter, Klebsiella, Legionella, Listeria, Morganella, Moraxella, Porphyromonas, Proteus, Providencia, Pseudomonas, Salmonella, Serratia, Shigella, Staphylococcus* spp., *Streptococcus* spp., *Treponema, Xanthomonas, Vibrio,* and *Yersinia*. Specific examples of such bacteria include *Vibrio harveyi, Vibrio cholerae, Vibrio parahemolyticus, Vibrio alginolyticus, Pseudomonas phosphoreum, Pseudomonas aeruginosa, Yersinia enterocolitica, Escherichia coli, Salmonella typhimurium, Haemophilus influenzae, Helicobacter pylori, Bacillus subtilis, Borrelia burgdorferi, Neisseria meningitidis, Neisseria gonorrhoeae, Yersinia pestis, Campylobacter jejuni, Mycobacterium tuberculosis, Streptococcus pneumoniae, Streptococcus pyogenes*, β-hemolytic streptococci, *Klebsiella pneumoniae, Burkholderia cepacia, Acinetobacter baumannii, Staphylococcus epidermidis*. The tebipenem formulations of this disclosure can be used to treat Gram-negative bacterial infections. In some embodiments, the Gram-negative bacterium is a *Pseudomonas*, e.g., *P. aeruginosa, Burkholderia*, or an *Acinetobacter*, e.g., *A. baumannii*.

In some embodiments the Gram-negative bacteria in the Enterobacterales order include *Escherichia coli, Klebsiella pneumoniae, Proteus mierabilis, Enterobacter cloacae, Citrobacter freundii, Citrobacter koseri, Klebsiella oxytoca, Providencia rettgeri, Klebsiella varicola, Serratia marcescens, Morganella morganii, Citrobacter braakii, Klebsiella aerogenes, Proteus hauseri, Providencia stuartii, Raoultella ornithinolytica, Enterobacter amnigenus, Enterobacter asburiae, Enterobacter bugandensis, Proteus penneri, Proteus vulgaris,* and *Serratia liquefaciens*.

In some embodiments, the Gram-negative bacterium is from the Enterobacteriaceae family, as family within the Enterobacterales order, e.g., *Klebsiella pneumonia*, e.g., *Escherichia coli*, e.g., *Enterobacter cloacae*, e.g., *Serratia marcescens*, e.g., *Salmonella typhimurium*, e.g., *Shigella dysenteriae*, e.g., *Proteus mirabilis*, e.g., *Citrobacter freundii*, e.g., *Yersinia pestis*.

In some embodiments the bacterial infection is caused by a Gram-positive bacterium, for example a *Enterococcus faecalis, Staphylococcus aureus*, Methicillin resistant *Staphylococcus aureus, Staphylococcus epidermidis*, Methicillin resistant *Staphylococcus epidermidis*, methicillin-susceptible coagulase-negative staphylococci (MSCoNS), *Staphylococcus saprophyticus, Enterococcus faecium, Staphylococcus lugdunensis, Enterococcus hirae, Streptococcus gallolyticus* bacterium, or Vancomycin-susceptible *Enterococcus faecalis*.

The tebipenem formulations of this disclosure can also be used to treat non-tubercular mycobacterial (NTM) infections. Examples of NTM pathogens include *M. fortuitum, M. chelonae-abscessus, M. avium* complex (MAC), *M. absces-*

*sus, M. intracellulare, M. ulcerans, M. chimaera, M. paratuberculosis, M. kansasii, M. marinum*, and *M. simiae*, and *M. scrofulaceum*.

In some embodiments, the infection is a polymicrobial infection, e.g., an infection comprising more than one organism. In some embodiments, the infection comprises at least one of the organisms listed above, e.g., one or more of *Pseudomonas*, e.g., *P. aeruginosa, Klebsiella*, e.g., *Klebsiella pneumoniae*, and/or *Acinetobacter*, e.g., *A. baumannii*.

The disclosure particularly includes methods of treating urinary tract infections, including complicated urinary tract infections, and pyelonephritis, including acute and chronic pyelonephritis in a patient comprising administering and effective amount of a tebipenem pivoxil formulation of this disclosure to the patient. UTIs and pyelonephritis are most commonly due to infection with *E. coli, K. pneumoniae*, or *P. mirabilis*.

In some embodiments the bacterial infection is a respiratory tract infection, for example a respiratory infection caused by a fastidious organism. For example the bacterial infection can be due to a *Citrobacter freundii* bacterial infection, a *Haemophilus influenze* infection, including a fluoroquinolone-resistant, β-lactamase-positive *Haemophilus influenze* infection, a β-lactamase-negative ampicillin-resistant [BLNAR]) *Haemophilus influenze* infection, a *Haemophilus* parainfluenza infection, a Methicillin-susceptible *Staphylococcus aureus* infection, a *Moraxella catarrhalis* infection, a Streptococcocus pyrogenes infection, or a *Streptococcus pneumoniae* infection, including a penicillin resistant *Streptococcus pneumoniae* infection. Tebipenem pivoxil has activity similar to ertapenem against tested respiratory bacterial pathogens except for Stretococcus *pneumoniae*. Tebipenem pivoxil displayed 8-fold greater activity against Stretococcus *pneumoniae* than ertapenem.

The disclosure includes a method of treating a bacterial infection in patient suffering from cancer. Gram negative infections such as ESBL bacterial pathogens and Enterobacterales and infections due to pathogens including *Citrobacter* species, *Enterobacter cloacae, Escherichia coli* including ESBL isolates, *Klebsiella pneumoniae, Proteus mirabilis, Serratia* species, ESBL *Klebsiella pneumoniae*, and *Enterobacter aerogenes* can be treated in patients with cancer by administering an effective amount of tebipenem pivoxil, for example as a tebipenem pivoxil formulation of the disclosure, to the patient.

The disclosure includes methods of treating a bloodstream infection in a patient comprising administering an effective amount of tebipenem pivoxil, for example as a tebipenem pivoxil formulation of the disclosure, to the patient. The bloodstream infection can be due to Enterobacterales bacterial pathogens, including an ESBL producing pathogen. The blood stream infection can be due to *E. coli* including *E. coli* of the ESBL phenotype, *K. pneumoniae*, including *K. pneumoniae* of the ESBL, MER-S, or MER-NS phenotypes. In some embodiments, the methods further include administering an additional active agent in combination with the dosage forms the disclosure, such as an antibiotic selected from the group consisting of but not limited to: beta-lactams such as penicillins, cephalosporins, carbacephems, cephamycins, carbapenems, monobactams, quinolones including fluoroquinolones and similar DNA synthesis inhibitors, tetracyclines, aminoglycosides, macrolides, glycopeptides, chloramphenicols, glycylcyclines, lincosamides, lipopeptides, lipodepsipeptides, such as daptomycin, and oxazolidinones.

In some embodiments, the bacterial infection is an upper and lower respiratory tract infection, pneumonia, bacteremia, a systemic infection, systemic inflammatory response syndrome, sepsis and septic shock, a urinary tract infection, a gastrointestinal infection, endocarditis, a bone infection, a joint infection, central nervous system infections such as meningitis, or an infection of the skin and soft tissue. The disclosure includes a method of treating Clostridioides *difficile* (*C. difficile*) by administering a dosage form of the disclosure to a patient in need of such treatment. The disclosure particularly includes a method of treating a complicated urinary tract infection in a patient. A "complicated urinary tract infection" is a clinical syndrome characterized by pyuria and a documented microbial pathogen on culture of urine blood, accompanied by local and systemic signs and symptoms, including fever (i.e., oral or tympanic temperature greater than 38 degrees Celsius), chills, malaise, flank pain, back pain, and/or costo-vertebral angle pain or tenderness, that occur in the presence of a functional or anatomical abnormality of the urinary tract or in the presence of catheterization.

The disclosure includes a method of treating pyelonephritis, including acute and chronic pyelonephritis. Pyelonephritis is a bacterial infection of the kidneys. It is characterized by inflammation of the renal pelvis and/or the parenchyma of the kidney due to bacterial infection. Symptoms of pyelonephritis include pain in back, side, or groin, fever, chills, nausea, vomiting, shaking, foul-smelling or discolored urine, and frequent need to urinate. In patients with pyelonephritis white blood cells and bacteria are present in the urine and the count of circulating white blood cells is increased.

NTMs are responsible for a number of conditions. This disclosure includes a method of treating a condition caused by NTM infection comprising administering a compound of the disclosure to a patient having such a condition. Such conditions include respiratory infection, lung infections, Johne's disease (in ruminants), Crohn's disease, osteomyelitis, peritonitis, pyelonephritis, cervical lymphadenitis, and disseminated infection in immunocompromised patients.

In some embodiments, the patient is a mammal, e.g., a human or non-human mammal. In some embodiments, the methods include treating one or more cells, e.g., cells in a culture dish.

In one aspect, the present disclosure features a method of treating a Gram-negative infection in a patient, the method comprising administering to said patient in need of such treatment a therapeutically effective amount of a compound described herein.

In other embodiments the disclosure includes treating an infection caused by Gram-positive bacteria, such as *Staphylococcus epidermidis* and *Staphylococcus aureus*.

In some embodiments, the patient is a trauma patient or a burn patient suffering from a burn or skin wound.

Tebipenem, an orally available carbapenem antibiotic, is as effective against bacterial pathogens as carbapenem antibiotics, such as ertapenem or meropenem, which can only be administered intravenously.

In a further aspect, the present disclosure features a method of reducing bacterial tolerance in a patient, the method comprising administering to said patient a therapeutically effective amount of a compound described herein.

In some embodiments, the method further includes identifying said patient suffering from an infection with bacteria resistant to antimicrobial therapy and treating the patient with tebipenem pivoxil HBr.

The tebipenem pivoxil HBr dosage can vary depending on factors such as the patient's illness and renal functional, though adjustments for age, body size, and sex are not needed for adult patients. Methods of treatment, for human subjects, include administering an oral dosage form containing 300 mg-800 mg tebipenem pivoxil per dosage form, in the form of tebipenem pivoxil HBr. In certain embodiments 600 mg tebipenem pivoxil HBr is given every 8 hours. Administration of tebipenem pivoxil HBr may continue for 6, 7, 9, 10, 11, 12, 13, 14, or 15 days, for 7-10 days, or for 14 days in the case of patients with bacteremia. Certain medical conditions affect the dosage of tebipenem pivoxil HBr that should be administered to a patient. For example, patients with renal impairment (RI), e.g. RI with creatine clearance <20 mL/min., or end-stage renal disease (ESRD) on hemodialysis (HD) have lower tebipenem clearance rates. For such patients the tebipenem pivoxil HBr dosage should be decreased. For example, the dose should be decreased to 300 mg tebipenem pivoxil q8h.

Pharmacokinetics

Tebipenem pivoxil HBr can be administered in fed or fasted conditions, including with a high-fat meal without a clinical effect on TBP exposure. $AUC_{0-t}$ and $AUC_\infty$ was comparable under fed and fasted conditions. TBP $C_{max}$ was approximately 13% lower after administration (as Formulation 13) under fed conditions. The median tebipenem pivoxil HBr $t_{max}$ was 1.00 hour in plasma and below the limit of quantitation with 12 hours of administration. $t_{1/2}$ in plasma and whole blood was 5.98 hours and 3.52 hours, respectively.

EXAMPLES

MATERIALS LIST

| Material | Compendium | Grade | Suppliers |
|---|---|---|---|
| Crospovidone | USP/NF, JP, Ph. Eur | POLYPLASDONE XL-10 | DKSH Japan |
| Magnesium stearate | USP/NF, JP, Ph. Eur | Mallinckrodt 5712 | Higuchi Inc. |
| Microcrystalline cellulose | USP/NF, JP, Ph. Eur | AVICEL PH-101 | SUN-A TEC |
| Microcrystalline cellulose | USP/NF | AVICEL PH-102 | |
| Microcrystalline cellulose | | PROSOLV SMCC 50 | JRS Pharma GmbH |
| Microcrystalline cellulose | | PROSOLV SMCC 90 | JRS Pharma GmbH |
| Silicon dioxide | USP/NF, JP | AEROSIL 200 | JUNSEI |
| OPADRY II | N/A | 85F91159 green | Colorcon |
| OPADRY | N/A | YS-1-7027 white | Colorcon |
| Purified Water | - | - | - |
| Tebipenem Pivoxil HBr | - | - | - |

Example 1. Tablet Cores Containing 45% (w/w) Tebipenem Pivoxil HBr

Tebipenem pivoxil HBR film-coated tablets of Examples 1-3 are manufactured according to the following generalized process.

Tebipenem pivoxil HBr is added to a bin blender. Crospovidone, if used, is also added to the bin blender.

Silicon dioxide is mixed manually with microcrystalline cellulose or a commercially available silicified microcrystalline cellulose, such as SMCC 50 or SMCC 90, is used.

The contents of the bin blender are blended, for example for 30-60 minutes at 8.0 rpm.

Magnesium stearate is then added to the bin blender. The Magnesium stearate can be pre-screened to ensure uniform size or otherwise treated prior to being added to the bin blender. The magnesium stearate is blended with the contents of the bin blender, for example for 3-10 minutes at 8.0 rpm.

The magnesium stearate containing blend is compressed using a rotary press to form the tablet cores. Cores can be coated with a functional or non-functional, such as Opadry II, in a coating pan. Cores are typically coated for a target of 3% w/w weight gain.

| Component | % tablet | Weight (mg/tablet) | % Tablet | Weight (mg/tablet) |
|---|---|---|---|---|
| Core tablet | | | | |
| Tebipenem Pivoxil HBr | 45.16 | 348.9[1] | 45.16 | 348.9 |
| Microcrystalline cellulose (AVICEL PH102), USP | 45.13 | 348.6 | 22.56 | 174.3 |
| Mannitol | 0 | 0 | 22.56 | 174.3 |
| Crospovidone (POLYPLASDONE XL-10), USP | 4.85 | 37.5 | 4.85 | 37.5 |
| Silicon dioxide (AEROSIL 200), USP | 0.97 | 7.5 | 0.97 | 7.5 |
| Magnesium stearate, USP | 0.97 | 7.5 | 0.97 | 7.5 |
| Sub-total | 97.1 | 750.0 | 97.1 | 750.0 |
| Coating | | | | |
| OPADRY YS-1-7027 white | 2.9 | 22.5 | 2.9 | 22.5 |
| Purified water, USP[1] | NA[1] | NA[1] | NA[1] | NA[1] |
| Total | 100.0 | 772.5 | 100.0 | 772.5 |

[1]Purified water removed during process

The numbers can also be viewed as a weight percent of the tablet core.

| Component | % tablet | Weight (mg/tablet) | % Tablet | Weight (mg/tablet) |
|---|---|---|---|---|
| Core tablet | | | | |
| Tebipenem Pivoxil HBr | 46.5 | 348.9 | 46.5 | 348.9 |
| Microcrystalline cellulose (AVICEL PH102), USP | 46.5 | 348.6 | 23.25 | 174.3 |
| Mannitol | 0 | 0 | 23.25 | 174.3 |
| Crospovidone (POLYPLASDONE XL-10), USP | 5.0 | 37.5 | 5.0 | 37.5 |
| Silicon dioxide (AEROSIL 200), USP | 1.0 | 7.5 | 1.0 | 7.5 |
| Magnesium stearate, USP | 1.0 | 7.5 | 1.0 | 7.5 |
| Sub-total | 97.1 | 750.0 | 97.1 | 750.0 |

Example 2. 300 mg Tebipenem Pivoxil Tablets with Reduced Crospovidone

The tablet cores of Examples 2 and 3 are prepared according to the following general procedure.

The tebipenem pivoxil HBr tablet cores are manufactured using a direct compression process with a two-step blending, followed by coating.

Tebipenem pivoxil HBr is passed through a mill equipped with a 0.457 mm screen at 1400 rpm into a container to deagglomerate the API. The milled tebipenem pivoxil HBr is then added to the bin blender. Crospovidone, if used, is added to the bin blender.

Silicon dioxide is mixed manually with microcrystalline cellulose or silicified microcrystalline cellulose is used. The mixture of silicon dioxide and microcrystalline cellulose (or SMCC) is processed to appropriate size, for example by passage through a mill (0.457 mm screen, 1400 rpm) into a container. This mixture is then added to the bin blender.

The tebipenem pivoxil HBr, crospovidone, and silicon dioxide/microcrystalline cellulose mixture are blended in the bin blender for 30-60 minutes at 8.0 rpm.

Magnesium stearate is screened, for example with a 0.261 mm screen) and then added to the bin blender. The blend is mixed for 3-10 minutes at 8.0 rpm.

The magnesium stearate containing blend is compressed using a rotary press to form the tablet cores. Cores can be coated for example with a film coating, in a coating pan for a target of 3% w/w weight gain.

| Component | Formulation 1 | | Formulation 2 | |
|---|---|---|---|---|
| | % tablet | Weight (mg/tablet) | % Tablet | Weight (mg/tablet) |
| Core tablet | | | | |
| Tebipenem Pivoxil HBr | 83.9 | 348.9[1] | 67.90 | 348.9 |
| Microcrystalline cellulose (AVICEL PH102), USP | 9.5 | 39.48 | 26.92 | 138.3 |
| Crospovidone (POLYPLASDONE XL-10), USP | 1.6 | 6.72 | 0.00 | 0 |
| Silicon dioxide (AEROSIL 200), USP | 1.0 | 4.03 | 0.97 | 4.984 |
| Magnesium stearate, USP | 1.0 | 4.03 | 1.21 | 6.23 |
| Sub-total | 97.0 | 403.0 | 97.0 | 498.4 |
| Coating | 3.0 | 12.5 | 3.0 | 12.4 |
| Total | 100.0 | 415.7 | 100.0 | 412.4 |

| Component | Formulation 1 | | Formulation 2 | |
|---|---|---|---|---|
| | % tablet | Weight (mg/tablet) | % Tablet | Weight (mg/tablet) |
| | Formulation 3 | | Formulation 4 | |
| | % tablet | Weight (mg/tablet) | % Tablet | Weight (mg/tablet) |
| Tebipenem Pivoxil HBr | 72.74 | 348.9 | 70.00 | 348.9 |
| Microcrystalline cellulose (AVICEL PH102), USP | 21.82 | 104.7 | 24.50 | 122.115 |
| Crospovidone (POLYPLASDONE XL-10), USP | 0 | 0 | 0 | 0 |
| Silicon dioxide (AEROSIL 200), USP | 0.97 | 4.652 | 1.20 | 5.981 |
| Magnesium stearate, USP | 1.45 | 6.978 | 1.40 | 6.978 |
| Sub-total | 97.0 | 465.2 | 97.1 | 484.0 |
| Coating | 3.0 | 14.4 | 2.9 | 14.5 |
| Total | 100.0 | 479.6 | 100.0 | 498.4 |

Example 3. 300 Mg Tebipenem Pivoxil HBr Tablets with Reduced Particle Size Microcrystalline Cellulose

| Component | Formulation 5 | | Formulation 6 | | Formulation 7 | |
|---|---|---|---|---|---|---|
| | % tablet | Weight (mg/tablet) | % tablet | Weight (mg/tablet) | % tablet | Weight (mg/tablet) |
| Core tablet | | | | | | |
| Tebipenem Pivoxil HBr | 69.99 | 348.9 | 70.0 | 348.9 | 70.0 | 348.9 |
| Microcrystalline cellulose (AVICEL PH101), USP | — | — | 20.0 | 99.7 | — | — |
| PROSOLV SMCC 50 | 20.0 | 99.7 | — | — | — | — |
| PROSOLV SMCC 90 | — | — | — | — | 21.0 | 104.7 |
| Crospovidone (POLYPLASDONE XL-10), USP | 4.90 | 24.4 | 4.9 | 24.4 | 4.9 | 24.4 |
| Silicon dioxide (AEROSIL 200), USP | 1.00 | 5.0 | 1.0 | 5.0 | 0 | 0.0 |
| Magnesium stearate, USP | 1.20 | 6.0 | 1.2 | 6.0 | 1.2 | 6.0 |
| Sub-total | 97.1 | 484.0 | 97.1 | 484.0 | 97.1 | 484.0 |
| Coating | 2.9 | 14.5 | 2.9 | 14.5 | 2.9 | 14.5 |
| Total | 100.0 | 498.5 | 100.0 | 498.5 | 100.0 | 498.5 |

Example 4. 300 mg Tebipenem Pivoxil HBr Tablets with Controlled API Particle Size The tebipenem pivoxil HBR film-coated tablet is manufactured using a direct compression process with a two-step blending, followed by coating. In this example the coating is a non-functional coating. The procedure for preparing a 50,000 tablet batch follows.

Tebipenem pivoxil HBr, 17.445 kg, is passed through a mill equipped with a 0.457 mm screen at 1400 rpm into a container to de-agglomerate the API. The milled tebipenem pivoxil HBr is then added to the bin blender.

Pre-de-agglomerated crospovidone, 0.24 kg, is added to the bin blender.

Silicon dioxide, 0.24 kg, is mixed manually with microcrystalline cellulose, 4.97 kg. The mixture of silicon dioxide and microcrystalline cellulose is passed through a mill (e.g. with a 0.457 mm screen at 1400 rpm) into a container. This mixture is then added to the bin blender.

The tebipenem pivoxil HBr, crospovidone, and silicon dioxide/microcrystalline cellulose mixture are blended in the bin blender for 30-60 minutes at 8.0 rpm.

Magnesium stearate, 0.31 kg, is passed through a 0.261 mm mesh and then added to the bin blender. The blend is mixed for 3-10 minutes at 8.0 rpm.

The magnesium stearate containing blend is compressed using a rotary press to form the tablet cores. Cores can be coated with coating (Opadry II) in a coating pan for a target of 3% w/w weight gain.

|  | Formulation 8/9 | | Formulation 10 | | Formulation 11 | |
| --- | --- | --- | --- | --- | --- | --- |
| Component | % Tablet | Weight (mg/tablet) | % tablet | Weight (mg/tablet) | % tablet | Weight (mg/tablet) |
| Core tablet | | | | | | |
| Tebipenem Pivoxil HBr | 71.9 | 348.9 | 75.0 | 348.9 | 74.0 | 348.9 |
| Microcrystalline cellulose (AVICEL PH101), USP | 20.0 | 97.1 | 20.0 | 93.1 | 20.0 | 94.4 |
| Crospovidone (POLYPLASDONE XL-10), USP | 3.0 | 14.6 | | 0.0 | 1.0 | 4.7 |
| Silicon dioxide (AEROSIL 200), USP | 1.0 | 4.9 | 1.0 | 4.7 | 1.0 | 4.7 |
| Magnesium stearate, USP | 1.2 | 5.8 | 1.2 | 5.1 | 1.1 | 5.1 |
| Sub-total | 97.1 | 471.2 | 97.1 | 451.742 | 97.1 | 457.9 |
| Coating | 2.9 | 14.1 | 2.9 | 13.5 | 2.9 | 13.7 |
| Total | 100.0 | 485.3 | 100.0 | 465.2 | 100.0 | 471.6 |

Formulation 12 was prepared using the protocol for Formulation 9-11. Tebipenem pivoxil HBr was sieved with a @0.610 screen, rotation speed 1400 rpm, to provide API having the desired particle size. Approximately 30-40% of particles passed through a 45 μm screen. Bulk density of API after sieving was between 0.25 g/mL and 0.31 g/mL. Bulk density of the Formulation 12 tablet core mixture was 0.385 g/cc, tapped density: 0.551 g/cc (200 tapped, 0.581 g/cc (400 tapped), 0.591 g/cc (600 tapped). The mixture exhibited a compressibility of 34.9%.

|  | Formulation 12 | |
| --- | --- | --- |
| Component | % Tablet | Weight (mg/tablet) |
| Core tablet | | |
| Tebipenem Pivoxil HBr | 73.0 | 348.9 |
| Microcrystalline cellulose (AVICEL PH101), USP | 20.8 | 99.4 |
| Crospovidone (POLYPLASDONE XL-10), USP | 1.0 | 4.78 |
| Silicon dioxide (AEROSIL 200), USP | 1.0 | 4.78 |
| Magnesium stearate, USP | 1.3 | 6.21 |
| Sub-total | 97.1 | 464.1 |
| Coating | 2.9 | 13.8 |
| Total | 100.0 | 477.9 |

Example 5. 300 Mg Tebipenem Pivoxil HBr Tablets with Controlled API Particle Size The required amount of crospovidone was weighed and passed through the Quadro Comil equipped with 1.143 mm screen at 1400 rpm. A portion of the microcrystalline cellulose, about 25-30%, was added to the required amount of silicon dioxide, manually mixed, and then passed through the Quadro Comil equipped with 1.143 mm screen at 1400 rpm. The remaining microcrystalline cellulose was passed through the Quadro Comil equipped with 1.143 mm screen at 1400 rpm. The required amount of tebipenem pivoxil HBr was weighed and passed through the Quadro Comil equipped with 1.143 mm screen at 1400 rpm.

The sieved materials were added to a 400 L bin blender in the following order: (1) tebipenem pivoxil HBr, (2) crospovidone, (3) mixture of silicon dioxide and microcrystalline cellulose, and (4) remaining microcrystalline cellulose. The mixture of sieved materials was blended for 60 minutes at 6.0 rpm to create the "blended mixture." Blend uniformity was confirmed at 15, 30, 45, and 60 minutes. adequate blend uniformity was achieved after 45 minutes.

Magnesium stearate was passed through the 261 μm mesh and added into the blended mixture in the bin blender. Blending was continued for an additional 10 minutes at 6.0 rpm to create the "lubricated blend."

The lubricated blend was compressed using a Kikusui 24 station rotary press. Tablets were formed using a Φ10.5 mm punch and WR 18/2.5 die. The press was operated at 30 rpm (or from 10-60 rpm), a precompression force of 2.5 kN (or 0-6 kN), and a force feeder speed of 20 rpm. The main compression force was adjusted to a target hardness of 110N (or 60-150 N).

Coating is applied by adding the required amount of OPADRY II to purified water. The coating dispersion was prepared using an agitator at 530 rpm for more than 12 hours. The core tablets are coated with the OPADRY II using a Freund Vector coating pan (Hi-Coater, HCF-100N). The coating step was deemed complete when the theoretical amount of the coating dispersion for the batch had been sprayed. The end point of the coating drying process was determined by LOD (loss on drying) analysis. The batch was deemed dry when the LOD was ≤2%.

| Component | Formulation 13 | |
|---|---|---|
| | % Tablet | Weight (mg/tablet) |
| Core tablet | | |
| Tebipenem Pivoxil HBr | 73.0 | 348.8 |
| Microcrystalline cellulose (AVICEL PH101), USP | 20.7 | 99.0 |
| Crospovidone (POLYPLASDONE XL-10), USP | 1.0 | 4.8 |
| Silicon dioxide (AEROSIL 200), USP | 1.0 | 4.8 |
| Magnesium stearate, USP | 1.3 | 6.2 |
| Sub-total | 97.0 | 463.6 |
| Coating | | |
| OPADRY II green (85F91159) | 3.0 | 14.3 |
| Total | 100.0 | 477.9 |

In an embodiment the Formulation 13 coated tablet (300 mg) is 10.5 mm. The Film Coat is prepared as a suspension in purified water and spray dried to weight gain of 3% w/w with respect to core table weight.

The tablet compositions for formulations 8-13 can also be viewed as a weight percent (% w/w) of the tablet core.

Example 7. Characterization of Formulations 8-11

The physical characteristics, weight, thickness, hardness, friability, disintegration time, and tableting pressure of Formulations 8-11 are provided in Tables 3-6. Tablets are formed using either an $\phi 11$ mm punch/die with embossing or an $\phi 9.5$ mm punch/die without emboss and a pre-compression force of 2.5 kN, and rotary tablet press speed of 25 rpm or 40 rpm. Tablet cores are compressed using an open feeder, punch sizes of $\phi 11$ mm (R12.75) with embossing and $\phi 9.5$ mm (R11) without embossing with compression pressures of 8 kN, 12 kN, 16 kN, 20 kN, 24 kN, and 28 kN. Higher main compression pressures, e.g. over 20 kN, resulted in over compression and unacceptable tablets in some instances. The core tablet weight, thickness, hardness, friability, and disintegration time were evaluated. Hardness is measured using a Toyama Sangyo (Sanjo, Japan) hardness tester, model TH303MP. Friability is measured using Toyama Sangyo model number TFT-120. Dissolution testing is conducted in accordance with USP<711>, Apparatus 2 (Paddle apparatus). The requirements are met if the quantities of active ingredients dissolved from the dosage units conform to USP <711> Acceptance Table 1. The dissolution media is sodium acetate buffer (approximately 22 mM), pH 5.0, Dissolution temperature is 37° C. Tebipenem pivoxil is quantitated via HPLC, UV detection at 330 nM.

| Component | Formulation 8/9 | | Formulation 10 | | Formulation 11 | | Formulation 12 | | Formulation 13 | |
|---|---|---|---|---|---|---|---|---|---|---|
| | % tablet | Weight (mg/tablet) | % tablet | Weight (mg/tablet) | % tablet | Weight (mg/tablet) | % tablet | Weight (mg/tablet) | % Tablet | Weight (mg/tablet) |
| Core tablet | | | | | | | | | | |
| Tebipenem Pivoxil HBr | 74.0 | 348.9 | 77.2 | 348.9 | 76.2 | 348.9 | 75.2 | 348.9 | 75.2 | 348.8 |
| Microcrystalline cellulose (AVICEL PH101), USP | 20.6 | 97.1 | 20.6 | 93.1 | 20.6 | 94.4 | 21.4 | 99.4 | 21.4 | 99.0 |
| Crospovidone (POLYPLASDONE XL-10), USP | 3.1 | 14.6 | — | 0.0 | 1.05 | 4.7 | 1.03 | 4.78 | 1.03 | 4.8 |
| Silicon dioxide (AEROSIL 200), USP | 1.05 | 4.9 | 1.05 | 4.7 | 1.05 | 4.7 | 1.03 | 4.78 | 1.03 | 4.8 |
| Magnesium stearate, USP | 1.25 | 5.8 | 1.25 | 5.1 | 1.2 | 5.1 | 1.33 | 6.21 | 1.33 | 6.2 |
| Total | 100.0 | 471.2 | 100.0 | 451.74 | 100.0 | 457.9 | 100.00 | 464.1 | 100.0 | 463.6 |

Example 6. Determination of Bulk and Tapped Densities of Core Blend Containing Magnesium Stearate Bulk density and tapped density of certain of the Magnesium stearate-containing blending were analyzed in accordance with the method of "USP <616> Method III—Measurement in a Vessel". The results are shown in Table 2.

TABLE 2

| | Form. 1 | Form. 6 | Form. 7 | Form. 8 | Form. 9 | Form. 10 | Form. 11 |
|---|---|---|---|---|---|---|---|
| Loose | 0.513 | 0.479 | 0.518 | 0.516 | 0.417 | 0.479 | 0.531 |
| 200 tapped | 0.652 | 0.675 | 0.700 | 0.698 | 0.615 | 0.659 | 0.703 |
| 400 tapped | 0.661 | 0.686 | 0.715 | 0.710 | 0.626 | 0.673 | 0.713 |
| 600 tapped | 0.673 | 0.697 | 0.723 | 0.718 | 0.633 | 0.677 | 0.720 |

TABLE 3

Characterization Core Tablets
(Formulation 8, φ9.5 mm, Compression speed: 25 rpm)

| Target compression pressure (kN) | 8 kN | 12 kN | 16 kN | 20 kN | 24 kN | 28 kN |
|---|---|---|---|---|---|---|
| Weight (mg) | 472.42 | 473.26 | 473.42 | 476.9 | 467.8 | 470.74 |
| Thickness (mm) | 6.286 | 6.07 | 5.998 | 5.974 | 5.90 | 5.924 |
| Hardness (N) | 94.8 | 141.2 | 170.8 | 189.6 | 171.8 | 170 |
| Friability (%) | 0 | 0 | 0 | 0 | Capping | Capping |
| Disintegration (sec) | — | — | — | — | — | — |
| Main compression pressure kN | 7.74 | 12.16 | 15.56 | 20.16 | 23.57 | 26.98 |

TABLE 4

Characterization Core Tablets
(Formulation 8, φ9.5 mm, Compression speed: 40 rpm)

| Target compression pressure (kN) | 8 kN | 12 kN | 16 kN | 20 kN | 24 kN | 28 kN |
|---|---|---|---|---|---|---|
| Weight (mg) | 472.52 | 471.82 | 471.2 | 471.9 | 476.9 | 475.94 |
| Thickness (mm) | 6.254 | 6.066 | 5.99 | 5.956 | 5.972 | 5.954 |
| Hardness (N) | 103.6 | 138.2 | 168.6 | 181.8 | 207.8 | 210.6 |
| Friability (%) | 0.02 | 0.03 | 0.03 | 0.06 | 0.00 | 0.03 |
| Disintegration (sec) | 20.7 | — | 27.5 | — | — | — |
| Main compression pressure (kN) | 8.01 | 11.8 | 15.6 | 19.3 | 24.09 | 26.17 |

TABLE 5

Characterization Core Tablets (Formulation 9, φ9.5 mm)

| Target compression pressure (kN) | 8 kN | 12 kN | 16 kN | 20 kN | 24 kN | 28 kN |
|---|---|---|---|---|---|---|
| Weight (mg) | 461.62 | 474.48 | 474.94 | 476.76 | 473.48 | 480.72 |
| Thickness (mm) | 6.222 | 6.092 | 6.006 | 6.014 | 5.972 | 5.966 |
| Hardness (N) | 114 | 173.8 | 217.6 | 254.4 | 224.6 | 249 |
| Friability (%) | 0 | 0.00 | 0.00 | 0.03 | 0.03 | 0.12 |
| Disintegration (sec) | 30.7 | — | — | 37 | — | — |
| Main compression pressure (kg) | 7.64 | 12.08 | 15.37 | 19.65 | 23.8 | 27.2 |

TABLE 6

Characterization Core Tablets (Formulation 10, φ9.5 mm)

| Target compression pressure (kN) | 8 kN | 12 kN | 16 kN | 20 kN | 24 kN | 28 kN |
|---|---|---|---|---|---|---|
| Weight (mg) | 456.9 | 460.34 | 457.98 | 456.62 | 452.42 | 453.98 |
| Thickness (mm) | 6.058 | 5.906 | 5.79 | 5.74 | 5.684 | 5.704 |
| Hardness (N) | 105.2 | 145.4 | 194 | 204.6 | 202.4 | 200.4 |
| Friability (%) | 0.04 | — | 0.12 | 0.07 | 0.00 | 0.23 |
| Disintegration (sec) | 44.8 | — | — | 939.5 | — | — |
| Main compression pressure (kN) | 8.01 | 12.04 | 15.89 | 19.98 | 23.69 | 30.12 |

TABLE 7

Characterization Core Tablets (Formulation 11, φ9.5 mm, 25 rpm)

| Target compression pressure (kN) | 8 kN | 12 kN | 16 kN | 20 kN | 24 kN | 28 kN |
|---|---|---|---|---|---|---|
| Weight (mg) | 463.86 | 463.6 | 464.5 | 463.96 | 463.72 | — |
| Thickness (mm) | 6.11 | 5.926 | 5.87 | 5.82 | 5.806 | — |
| Hardness (N) | 108 | 152 | 178.8 | 193.6 | 189.8 | — |
| Friability (%) | 0.03 | 0.06 | 0.03 | 0.03 | Capping | — |
| Disintegration (sec) | 21.8 | — | — | 27.8 | — | — |
| Main compression pressure (kN) | 7.99 | 12.054 | 16.21 | 19.75 | 23.52 | — |

TABLE 8

Characterization Core Tablets (Formulation 11, φ9.5 mm, Compression speed: 40 rpm)

| Target compression pressure (kN) | 8 kN | 12 kN | 16 kN | 20 kN | 24 kN | 28 kN |
|---|---|---|---|---|---|---|
| Weight (mg) | 465.38 | 465.52 | 467.56 | 464.88 | — | — |
| Thickness (mm) | 6.19 | 5.978 | 5.904 | 5.862 | — | — |
| Hardness (N) | 95.6 | 141 | 174.8 | 176.6 | — | — |
| Friability (%) | 0.00 | 0 | 0.02 | Capping | — | — |
| Disintegration (sec) | 20.5 | — | 22 | — | — | — |
| Main compression pressure (kN) | 7.84 | 12.05 | 16.02 | 19.36 | 25.00 | — |

Example 8. Activity of Oral Tebipenem Against Resistant *E. coli* from Urinary Tract Infections The study assessed the prevalence of resistance and evaluated the activity of oral tebipenem (TBP) and comparators against EC from urinary tract infections. Samples were collected in 2020 from 18 EU countries.

764 *E. coli* samples were collected from UTIs as part of the STEWARD surveillance program and centrally tested for susceptibility (S) to tebipenem pivoxil (TBP) and comparator agents. Results were interpreted using EUCAST criteria. No criteria are yet available for Tebipenem pivoxil. ESBL phenotypes were determined by CLSI criteria and sequenced to identify CTX-M-15 genotype and clonal complex ST131. Activity of tebipenem pivoxil and comparators was assessed against different resistant phenotypes/genotypes.

The prevalence of ESBL, levofloxacin (LEV)-resistant (R) and TMP-SMX-R phenotypes were 16.5%, 20.6% and 30.1%, respectively, for all *E. coli*. Among ESBL phenotypes, high co-resistance rates of >60% to LEV and/or TMP-SMX were observed. Among all *E. coli*, the $MIC_{90}$s for TBP, ertapenem (ETP) and meropenem (MER) were 0.015, 0.03 and 0.03 μg/mL, respectively. Susceptibility rates for ETP and MER were 99.9% and 100%, respectively. The $MIC_{90}$ for mecillinam (MEC) was >8 μg/mL and 88.0% of *E. coli* were susceptible. TBP exhibited similar activity against LEV-R, TMP-SMX-R and multidrug resistant phenotypes with $MIC_{90}$ values of ≤0.03 μg/mL, regardless of resistance phenotype. Among EC ST131 and genotypes positive for CTM-M-15 alone and in combination with other β-lactamases the $MIC_{90}$ for TBP was 0.03 μg/mL.

The study verified that ESBL *E. coli* from UTI exhibit high co-resistance to oral LEV and TMP-SMX, and that such infections can effectively be treated with oral tebipenem pivoxil, including the oral tebipenem pivoxil formulations of this disclosure. Tebipenem pivoxil exhibits similar activity to ETP and MER based on $MIC_{90}$ comparison against all *E. coli* from UTI including ESBL, LEV-R, TMP-SMX-R and MDR phenotypes. TBP retains activity against EC ST131 and CTX-M-15 that are prevalent in UTIs worldwide.

Example 9. Efficacy of Tebipenem Pivoxil Hydrobromide in Patients with Complicated Urinary Tract Infection and/or Acute Pyelonephritis and Associated Bacteremia The objective of this analysis was to evaluate the efficacy of TBP-PI-HBr in the subset of patients with associated bacteremia from a study of patients with either cUTI or acute pyelonephritis.

At baseline, 100 (11.6%) patients in the study population had bacteremia at baseline. Across both treatment groups, the predominant blood isolates were *E. coli* (71.0%) and *E. faecalis* (15.0%). Up to 33.3% of Enterobacterales blood isolates had ≥1 antibiotic-resistant phenotypes (extended-spectrum β-lactamase [ESBL]-producing, fluoroquinolone-non-susceptible, and/or trimethoprim-sulfamethoxazole [TMP-SMX]-resistant). Overall response rates among TBP-PI-HBr- and ertapenem-treated patients with bacteremia were 93.6% and 96.2% at the end-of-treatment (EOT), respectively, and were 72.3% and 66.0%, respectively, at test-of-cure (TOC). Clinical cure rates were 100% in both treatment groups at EOT, 97.9% and 94.3% for TBP-PI-HBr and ertapenem, respectively, at test of cure (TOC) and were approximately 89% in both treatment groups at the late-follow-up (LFU) visit. Clinical and microbiological response rates among patients infected with drug-resistant blood isolates were similar between treatment groups at each visit. Oral TBP-PI-HBr monotherapy administered up to 14 days appeared effective in the treatment of bacteremia secondary to cUTI/AP, with response rates similar to that of IV ertapenem, including patients with resistant Gram-negative uropathogens.

Example 10. Efficacy of Tebipenem Pivoxil HBr Against Antibiotic Resistant E. coli Strains A total of 2,395 E. coli strains recovered from urine samples obtained in 2018, 2019, or 2020 from patients with cUTI/AP were subjected to genome sequencing, followed by screening of extended-spectrum β-lactamase (ESBL) genes and epidemiology typing (MLST).

A total of 16.1%, 15.4% and 14.6% of EC met the ESBL screening criteria in 2018, 2019 and 2020, respectively. 269/360 (74.7%) carried blaCTX-M and 2/360 (0.6%) had blaSHV-12. blaCMY (33/360; 9.2%) was the most common cephalosporinase, followed by blaDHA (7/360; 1.9%). A CRE phenotype, which carried blaKPC-2, was found in one isolate. Acquired genes were not detected in 56 strains. 50 ST types were noted in isolates that met the ESBL criteria screening, with the majority of isolates being ST131 (56.2%). 21 (6.7%) and 19 (6.0%) isolates belonged to ST38 and ST1193, respectively, followed by ST represented by 8 or less isolates. Among ST131, 56.5% carried blaCTX-M from group 1 and 35.6% had genes associated with group 9. Overall, tebipenem pivoxil HBr showed consistent MIC50 values throughout the subsets. ERT had activity (≥97.0% susceptible) against the various subsets; however, lower susceptibility rates (85.7-90.6%) were noted against isolates carrying plasmid AmpC. Other agents (ceftriaxone and cefazolin) had activity only against non-ESBL producers.

blaCTX-M comprised the majority of acquired genes detected among extended spectrum β-lactamase (ESBL) strains, which belonged mostly to ST131, emphasizing the expansion of this clone. The data from this study is summarized in Table 9. In Table 9, TBP is tebipenem pivoxil, ERT is ertapenem, CRO is ceftriaxone, CFZ is cefazolin and A/C is amoxicillin-clavulanate (2:1). CTM[a] includes $bla_{CTX-M-15}$; 86 $bla_{CTX-M-27}$; 9 $bla_{CTX-M}$-55; and 2 isolates with a distinct $bla_{CTX-M}$ allele. CMY[b] includes 5 isolates with concomitant $bla_{CTX-M}$ and 1 isolate with $bla_{CHA}$.

experiments for tebipenem, imipenem, ertapenem, and ceftazidime. These isolates demonstrated a general susceptible phenotype toward broad-spectrum β-lactam agents and represented isolates with stable and baseline production of AmpC (data not shown).

A second set of 36 Enterobacterales and 32 P. aeruginosa clinical isolates with proven overexpression of AmpC by qRT-PCR (i.e. expression >10-fold higher than a susceptible control) were tested for susceptibility as well. These isolates were recovered from patients with documented infections during 2010-2019 (55.8% from 2015-2019) and sent to a central monitoring laboratory (JMI Laboratories, North Liberty, IA, USA) as part of the SENTRY Antimicrobial Surveillance Program. Bacterial identification was confirmed by standard algorithms supported by matrix assisted laser desorption ionization-time of flight mass spectrometry (Bruker Daltonics, Bremen, Germany).

For susceptibility testing isolates were tested for susceptibility by broth microdilution following the Clinical and Laboratory Standards Institute (CLSI) M07 (2018) guidelines. Frozen-form broth microdilution panels were manufactured by JMI Laboratories and contained cation-adjusted Mueller-Hinton broth. Quality assurance was performed by sterility checks, colony counts, and testing CLSI recommended quality control reference strains.

AmpC induction was determined as follows. Baseline MIC values were determined by broth microdilution method, as described above, for 9 Gram-negative isolates with basal expression of ampC. These isolates were cultured overnight on blood agar plates. A standardized inoculum made from fresh overnight plate cultures was added to flasks containing 50 mL of Luria-Bertani (LB) broth and incubated by shaking at 37° C. to $OD_{600}$ of 0.3. Upon reaching the exponential growth phase, each organism culture was split into multiple flasks with each testing drug (tebipenem, ceftazidime, ertapenem, and imipenem) added to various final concentrations (0×, 0.25×, 1×, 4×, and 16×) of the

TABLE 9

| Phenotype/ genotype (No. of isolates) | MIC$_{50}$/MIC$_{90}$ in μg/mL (% susceptible by CLSI M100 criteria) | | | | |
|---|---|---|---|---|---|
| | TBP | ERT | CRO | CFZ | A/C |
| Non-ESBL (2035) | 0.015/ 0.015 (-) | ≤0.008/ 0.015 (100) | ≤0.06/ 0.12 (100) | 2/8(96.4) | 4/16(86.6) |
| ESBL (360) | 0.015/ 0.03 (-) | 0.03/ 0.12(97.4) | >8/ >8(6.4) | >32/ >32(0.6) | 16/32(47.2) |
| CTX-M a | 0.015/ 0.03 (-) | 0.03/ 0.12(98.9) | >8/ >8(0.0) | >32/ >32(0.0) | 8/16(57.6) |
| CMYb (33) | 0.015/ 0.03 (-) | 0.06/ 0.12(90.6) | >8/ >8(0.0) | >32/ >32(0.0) | >32/ >32(3.0) |
| DHA(7) | 0.03/- (-) | 0.06/-(85.7) | 2/-(28.6) | >32/-(0.0) | >32/-(0.0) |
| ST131 (222) | 0.015/ 0.03 (-) | 0.03/ 0.06(99.1) | >8/ >8(20.3) | >32/ >32(17.4) | 8/16(54.6) |
| Non-ST131 (203) | 0.015/ 0.03 (-) | 0.015/ 0.12(97.0) | >8/>8(37.9) | >32/ >32(30.5) | 8/ >32(55.2) |

Example 11. Effect of Tebipenem Pivoxil HBr on Enterobacterales and Pseudomonas aeruginosa Overexpressing AMPC Imipenem is considered a strong AmpC inducer even though carbapenems are not AmpC substrates. This example investigates AmpC induction in several bacterial pathogens by tebipenem and other carbapenems and the susceptibility of bacterial pathogens overexpressing AmpC to tebipenem.

A total of 8 Enterobacterales species and 1 Pseudomonas aeruginosa isolate were selected for the AmpC induction respective baseline MIC. These cultures were incubated under shaking conditions. A 40 mL aliquot of bacterial cultures was sampled at time 0 and 2 hours after drug exposures. Each sample aliquot was harvested by centrifugation and the supernatant was discarded.

Protein crude extract preparations were made in 200 μL of BugBusterR (Novagen, Darmstadt, Germany) per manufacturer instructions and cell debris was removed by centrifugation. Protein concentrations were determined in each crude extract by standard methodologies.

AmpC induction was measured by the intensity of β-lactamase hydrolytic activity against 0.1 mM nitrocefin in 0.1 M phosphate buffer at pH 7.0 using spectrophotometry at 482 nm (Δ absorbance/minute/mg of protein). The drug exposure conditions that caused a >4-fold increase in hydrolysis activity compared to the baseline were subjected to postinduction experiments. Briefly, cells were grown under the same conditions as before and tested for susceptibility by broth microdilution.

In general, tebipenem and imipenem increased production of AmpC among all Enterobacterales, except for *C. koseri* and *S. marcescens* (data not shown). Exposure to ertapenem and ceftazidime did not seem to affect production of AmpC among the Enterobacterales species tested. The induction experiments performed showed that exposure to tebipenem promote increased production of AmpC in Enterobacterales. However, imipenem seemed to be, in general, an AmpC inducer stronger than tebipenem. The AmpC induction phenomenon seemed to be species dependent for both tebipenem and imipenem, since negative or inconsistent results gests that the production of AmpC induced in these isolates was not elevated enough to cause a shift in MIC.

When tested against the second set of Enterobacterales overproducing AmpC (>10-fold higher than a susceptible control) according to qRT-PCR experiments, tebipenem ($MIC_{50/90}$, 0.03/0.25 μg/mL) inhibited all isolates at ≤1 μg/mL (Table 10). Tebipenem and meropenem ($MIC_{50/90}$, 0.03/0.12 μg/mL) $MIC_{50}$ and $MIC_{90}$ results obtained against this Enterobacterales collection were similar. These MIC results for tebipenem and meropenem were at least 2- to 4-fold lower than those for ertapenem ($MIC_{50/90}$, 0.12/2 μg/mL) and imipenem (MIC50/90, 0.25/0.5 μg/mL). Tebipenem showed MIC50 and MIC90 results of 4 and 4 g/mL, respectively, against *P. aeruginosa* isolates that overproduced AmpC (Table 10).

Tebipenem showed potent activity against Enterobacterales with confirmed overproduction of AmpC. The tebipenem antimicrobial potency was similar to that observed for meropenem, both of which were greater than those noted for imipenem and ertapenem.

TABLE 10

| Antimicrobial agent | MIC (μ/ml) | | | CLSI | | |
|---|---|---|---|---|---|---|
| | $MIC_{50}$ | $MIC_{90}$ | MIC range | % S | %1 | % R |
| Enterobacterales (36) | | | | | | |
| Tebipenem | 0.03 | 0.25 | 0.015 to 1 | NA | NA | NA |
| Ertapenem | 0.12 | 2 | 0.015 to >2 | 80.6 | 8.3 | 11.1 |
| Imipenem | 0.25 | 0.5 | ≤0.12 to 1 | 100.0 | 0.0 | 0.0 |
| Meropenem | 0.03 | 0.12 | ≤0.015 to 1 | 100.0 | 0.0 | 0.0 |
| Amoxicillin-clavulanic acid | >32 | >32 | 8 to >32 | 2.8 | 11.1 | 86.1 |
| Aztreonam | >16 | >16 | 2 to >16 | 31.4 | 14.3 | 54.3 |
| Cefepime | 0.5 | 128 | 0.03 to >256 | 68.6 | 8.6 | 22.9 |
| Ceftazdime | 32 | >32 | 1 to >32 | 28.6 | 11.4 | 60.0 |
| Ceftriaxone | >8 | >8 | 0.25 to >8 | 22.2 | 13.9 | 63.9 |
| Cefuroxime | >64 | >64 | 16 to >64 | $0.0^b$ | 5.6 | 94.4 |
| | | | | $0.0^c$ | 5.6 | 94.4 |
| Ciprofloxacin | 0.12 | >16 | ≤0.03 to >16 | 55.6 | 2.8 | 41.7 |
| Piperacillin-tazobactam | 32 | >128 | 4 to >128 | 47.2 | 19.4 | 33.3 |
| Tetracycline | 4 | >16 | 1 to >16 | 50.0 | 5.6 | 44.4 |
| Tigecycline | 0.25 | 1 | ≤0.06 to 4 | $94.4^d$ | 5.6 | 0.0 |
| *P. aeruginosa* (32) | | | | | | |
| Tebipenem | 4 | 4 | 2 to 8 | NA | NA | NA |
| Ertapenem | >2 | >2 | 2 to >2 | NA | NA | NA |
| Imipenem | 1 | 2 | 0.5 to 8 | 96.9 | 0.0 | 3.1 |
| Meropenem | 0.5 | 1 | 0.12 to 2 | 100.0 | 0.0 | 0.0 |
| Aztreonam | 16 | >16 | 4 to >16 | 18.8 | 31.2 | 50.0 |
| Cefepime | 16 | 32 | 4 to >256 | 46.9 | 40.6 | 12.5 |
| Ceftazdime | 32 | >32 | 4 to >32 | 15.6 | 12.5 | 71.9 |
| Ceftriaxone | >8 | >8 | >8 to >8 | NA | NA | NA |
| Ciprofloxacin | 0.12 | 16 | 0.06 to >16 | 68.8 | 6.2 | 25.0 |
| Piperacillin-tazobactam | 128 | >128 | 8 to >128 | 6.2 | 40.6 | 53.1 | were obtained for *C. koseri* and *S. marcescens*. Exposure to imipenem, followed by ceftazidime and tebipenem, promoted increased production of AmpC in *P. aeruginosa*. Tebipenem, imipenem, and ceftazidime increased the production of AmpC in *P. aeruginosa* after exposure. The same effect over *P. aeruginosa* was not observed with ertapenem.

Bacterial cells with confirmed increased presence of AmpC after drug exposure did not show increased MIC (i.e., >4-fold) to antimicrobial agents when compared to baseline values (data not shown). Enterobacterales or *P. aeruginosa* cells showing increased production of AmpC after drug exposure did not display increased MIC when compared to the respective baseline counterpart. This observation sug- Example 12. In Vitro Activity of Tebipenem Pivoxil Against Gram-Positive Clinical Isolates The purpose of this study was to investigate the in vitro activity of tebipenem and comparator agents, including ertapenem and meropenem, against a recent collection of Gram-positive isolates associated with clinical infections. The susceptibility of 580 Gram-positive organisms were tested, including: Methicillin-susceptible *Staphylococcus aureus* (MSSA, 489 isolates), Methicillin-susceptible *Staphylococcus epidermidis* (MSSE, 31), other methicillin-susceptible coagulase-negative staphylococci (MSCONS, 29), and Vancomycin-susceptible *Enterococcus faecalis*

(31). Bacterial species were identified by JMI Laboratories using standard microbiology methods and matrix-assisted laser desorption ionization-time of flight mass spectrometry (Bruker Daltonics, Bremen, Germany). The isolates were collected in 2018 and 2019 as part of the SENTRY surveillance program and selected to be representative of these species with 45.0% from the United States, 44.3% from Europe, 5.3% from the Asia-Pacific region, and 5.3% from Latin America. Isolates are primarily from pneumonia in hospitalized patients (498 isolates; 85.9%), urinary tract infections (42 isolates; 7.2%), and bloodstream infections (38 isolates; 6.6%). Isolates were tested in a central laboratory (JMI Laboratories) for antimicrobial susceptibility using the CLSI M07 (2018) reference broth microdilution method. JMI Laboratories produced frozen-form 96-well panels and used cation-adjusted Mueller-Hinton broth (CA-MHB) as the testing medium. All categorical interpretations used CLSI M100 (2021) and EUCAST v10.0 (2021) breakpoint criteria, where published. Quality control organisms include *Escherichia coli* ATCC 25922, *Escherichia coli* ATCC 35218, *Enterococcus faecalis* ATCC 29212, *Pseudomonas aeruginosa* ATCC 27853, and *Staphylococcus aureus* ATCC 29213 were tested concurrently with clinical isolates.

Activity of tebipenem pivoxil against MSSA isolates is as follows. Tebipenem had an $MIC_{50/90}$ value of 0.015/0.03 mg/L. Tebipenem had the lowest $MIC_{50/90}$ results of all antimicrobial agents tested (Ertapenem, trimethoprim-sulfamethoxazole, levofloxacin, tetracycline, erythromycin, gentamycin). Tebipenem $MIC_{90}$ value was 8-fold lower than ertapenem ($MIC_{90}$, 0.25 mg/L) against MSSA. Most comparator agents tested showed susceptibility rates ≥90.0% against MSSA isolates, except for erythromycin, which was 65.6% susceptible.

Activity against MSSE isolates is as follows. Tebipenem had an MIC50/90 value of 0.008/0.015 mg/L. Tebipenem had the lowest $MIC_{50/90}$ results of all antimicrobial agents tested. Tebipenem $MIC_{90}$ value was 32-fold lower than ertapenem ($MIC_{90}$, 0.5 mg/L) against MSSE. Most comparator agents tested showed susceptibility rates ≥90.0% against MSSE isolates, except for erythromycin, which was 54.8% susceptible.

Activity against MSCONS species other than *S. epidermidis* is as follows. Tebipenem had an $MIC_{50/90}$ value of 0.015/0.03 mg/L. Tebipenem had the lowest $MIC_{50/90}$ results of all antimicrobial agents tested. Tebipenem $MIC_{90}$ value was 32-fold lower than ertapenem ($MIC_{90}$, 1 mg/L) against other MSCONS. All other MSCONS isolates were susceptible to ertapenem and amoxicillin clavulanic acid whereas susceptibilities to trimethoprim-sulfamethoxazole (83.9% S) and erythromycin (54.8% S) were lower.

Activity against *E. faecalis* is as follows. Tebipenem inhibited all *E. faecalis* isolates at ≤1 mg/L ($MIC_{90}$, 1 mg/L). This $MIC_{90}$ value was at least 2-fold lower than meropenem ($MIC_{90}$, >1 mg/L) and 16-fold lower than ertapenem ($MIC_{90}$, >8 mg/L). Susceptibility rates of 80.6% and 100.0% were observed for levofloxacin and ampicillin, respectively, against *E. faecalis* isolates.

Tebipenem displayed potent activity against methicillin-susceptible staphylococci, including MSSA, MSSE, and other MSCONS. Tebipenem $MIC_{50}$ and $MIC_{90}$ values for these species and species groups ranged from 0.015-0.03 mg/L and the activity observed was 16- to 32-fold greater than ertapenem.

The in vitro activity of tebipenem (all isolates with MIC values ≤1 mg/L) was greater than meropenem and ertapenem against *E. faecalis* isolates. These data indicate that tebipenem is an option for treating urinary tract infections caused by these organisms or as an empiric option to provide broader coverage against Gram-negative and -positive organisms.

Example 13. Tebipenem In Vitro Activity Against a Collection of Pathogens Responsible for Urinary Tract Infections in the United States This study assessed the in vitro activity of tebipenem and comparator agents against Enterobacterales (ENT) responsible for UTIs in the US during 2019-2020. A total of 3,576 ENT recovered from urine samples during the 2019-2020 STEWARD Surveillance Program were included in the study. Isolates were collected from medical centers in all 9 US Census Regions and were centrally tested for susceptibility by reference broth microdilution method. MIC interpretation was performed based on CLSI criteria.

*E. coli* (EC) comprised 65.6% of all ENT pathogens, *K. pneumoniae* (KPN) (14.3%), *P. mirabilis* (PM) (6.6%), and other species (13.7%). Tebipenem ($MIC_{90}$, 0.015-0.06 mg/L) and ertapenem (ERT; $MIC_{90}$, 0.03 mg/L) showed similar $MIC_{90}$ results against ENT, EC, and KPN (see Table 11 below). Ceftazidime (CAZ; $MIC_{90}$, 8-16 mg/L) had elevated $MIC_{90}$ values and suboptimal susceptibility results (86.1-89.3%) against ENT, EC, and KPN. The oral agents, cefuroxime, amoxicillin-clavulanate, TMP-SMX, and levofloxacin showed susceptibility rates ranging from 63.1% to 87.1% against ENT, EC, and KPN. TBP ($MIC_{50/90}$, 0.12/0.12 mg/L) inhibited all PM at 0.25 mg/L. PM isolates were susceptible to ERT (100.0%), CAZ (98.7%), cefuroxime (94.4%), and amoxicillin/clavulanate (96.6%), whereas susceptibility rates of 71.8-76.8% were noted for TMP-SMX and levofloxacin.

TABLE 11

| | MIC values of different agents against various UTI-causing organisms | | | | | | |
|---|---|---|---|---|---|---|---|
| | $MIC_{50}/MIC_{90}$ in mg/mL (% susceptible; CLSI) | | | | | | |
| Organism | Tebipenem[a] | Ertapenem | Ceftazidime | Cefuroxime[b] | A/C | TMP-SMX | Levofloxacin |
| All (3,567) | 0.015-0.06 | ≤0.008/0.03 (98.5) | 0.25/8 (88.1%) | 4/>64 (63.5) | 4/32 (76.1) | ≤0.12/>4 (73.9) | 0.06/16 (79.4) |
| *E. coli* (2,339) | 0.015/0.015 | ≤0.008/0.03 (99.6) | 0.25/8 (89.3) | 4/>64 (63.1) | 4/16 (80.8) | ≤0.12/>4 (69.2) | 0.03/16 (75.7) |
| *K. pneumoniae* (511) | 0.015/0.03 | ≤0.008/0.03 (96.3) | 0.25/16 (86.1) | 4/>64 (75.3) | 2/16 (86.7) | ≤0.12/>4 (79.8) | 0.06/1 (87.1) |

TABLE 11-continued

MIC values of different agents against various UTI-causing organisms

| | MIC$_{50}$/MIC$_{90}$ in mg/mL (% susceptible; CLSI) | | | | | | |
|---|---|---|---|---|---|---|---|
| Organism | Tebipenem[a] | Ertapenem | Ceftazidime | Cefuroxime[b] | A/C | TMP-SMX | Levofloxacin |
| P. mirabilis (235) | 0.12/0.12 | 0.15/0.15 (100.0) | 0.06/0.12 (98.7) | 1/4 (94.4) | 1/1 (96.6) | ≤0.12/>4 (76.8) | 0.06/16 (71.8) |

A/C, amoxicillin/clavulanate;
TMP-SMX, trimethoprim-sulfamethoxazole
[a]Breakpoint not available.
[b]Percent susceptible based on the oral breakpoint.

This study showed TBP displayed potent activity against ENT UTI pathogens recovered from patients in the US. TBP demonstrated in vitro activity against these UTI pathogens similar to that of ERT. In addition, these data showed compromised activity of intravenous and oral agents used for treating UTI. This data demonstrates tebipenem as an effective oral option for management of UTI in the US.

Example 14. In Vitro Activity of Tebipenem Against Characterized Subsets of Urinary Tract Infection-Causing *Escherichia coli*

A total of 2,395 *E. coli* recovered from urine samples during the 2018-2020 STEWARD Surveillance Program were included. Isolates were collected from medical centers in all 9 US Census Regions and tested by broth microdilution. MIC interpretation was based on CLSI. Isolates that met MIC criteria were subjected to genome sequencing, followed by screening of extended-spectrum b-lactamase (ESBL) genes and epidemiology typing (MLST).

A total of 16.1%, 15.4% and 14.6% of *E. coli* met the ESBL screening criteria in 2018, 2019 and 2020, respectively. 269/360 (74.7%) carried blaCTX-M and 2/360 (0.6%) had blaSHV-12. blaCMY (33/360; 9.2%) was the most common cephalosporinase, followed by blaDHA (7/360; 1.9%). A CRE phenotype was noted in 1 isolate from New York, which carried blaKPC-2. Acquired genes were not detected in 56 strains. 50 ST types were noted in isolates that met the ESBL criteria screening, with the majority of isolates being ST131 (56.2%). 21 (6.7%) and 19 (6.0%) isolates belonged to ST38 and ST1193, respectively, followed by STs represented by 8 or less isolates. Among ST131, 56.5% carried blaCTX-M from group 1 and 35.6% had genes associated with group 9.

Overall, TBP showed consistent MIC$_{50}$ values throughout the subsets. ERT had activity (≥97.0% susceptible) against the various subsets; however, lower susceptibility rates (85.7-90.6%) were noted against isolates carrying plasmid AmpC. Other agents (ceftriaxone and cefazolin) had activity only against non-ESBL producers.

Example 15. An Open-Label, Randomized, Single-Dose, Semi-Replicate, 4-Period, Crossover, Bioequivalence Study Comparing Two Tablet Formulations of Tebipenem Pivoxil Hydrobromide (TBPM-PI-HBr) in Healthy Adult Subjects

TABLE 12

TBP-PI-HBr Oral tablet immediate release compositions of Tablets A and B

| Ingredient | Amount in Tablet A | Amount in Tablet B (mg)[a] (Formulation 13) |
|---|---|---|
| Drug Substance | | |
| TBP-PI-HBr | 348.9[b] | 348.8[b,c] |
| Excipients | | |
| Microcrystalline Cellulose | 348.6[d] | 99.0[d] |
| Crospovidone | 37.5 | 4.8 |
| Silicon dioxide | 7.5 | 4.8 |
| Magnesium Stearate | 7.5 | 6.2 |
| Film Coating | | |
| OPADRY white (YS-1-7027) | 22.5[e] | NA |
| OPADRY II green (85F91159) | NA | 14.3[e] |
| Purified water | NA[f] | NA[f] |
| Total | 772.5 | 477.9 |

[a]Tablet B is 10.5 mm in diameter.
[b]Equivalent to 300 mg tebipenem pivoxil free base.
[c]Quantity to be corrected from potency assay. Weight represent 100% theoretical potency.
[d]The amount of microcrystalline cellulose is adjusted in formulation based on the actual amount of TBP-PI-HBR.
[e] Film Coat is prepared as a suspension in purified water and spray dried to a weight gain of 3% w/w with respect to tablet core weight.
[f]Purified water is removed during process and does not appear in the final product.
NA, not applicable. TBP-PI-HBr, tebipenem pivoxil hydrobromide.

A new TBPM-PI-HBr tablet formulation ("Tablet B") was developed to reduce the tablet size by decreasing excipient content, thus increasing percent drug load while maintaining a 300 mg dose of TBPM-PI per tablet. The objectives of this study were to assess the bioequivalence (BE) of two tablet formulations of TBPM-PI-HBr in healthy adult subjects under fasted conditions, and to assess the effect of food on the PK of TBPM following administration of TBPM-PI-HBr as Tablet B. The two tablet formulations were clinical trial tablet formulation ("Tablet A") and reduced size formulation ("Tablet B").

In addition, while food was shown not to have an effect on the bioavailability (AUC) of the Tablet A formulation the effect of a FDA standard high-fat/high-calorie meal ("fed conditions") on the bioavailability of TBPM-PI-HBr as the reduced size formulation ("Tablet B") was assessed. As a secondary objective, the food-drug interactions of TBPM- PI-HBr the Tablet B formulation were evaluated since these can have a significant impact on the safety and efficacy of the drug.

TABLE 13

STUDY OBJECTIVES AND ENDPOINTS

| Objectives | Endpoints |
|---|---|
| Primary | |
| To assess the BE of two tablet formulations of TBPM-PI-HBr administered as a single oral dose under fasted conditions in healthy adult subjects. | The primary PK parameters of TBPMwere: AUC0-inf, AUC0-t, and Cmax. The secondary PK parameters were: Tmax, t½, and Kel. |
| Secondary | |
| To characterize the effect of food on the PK of TBPM when administered as the TBPM-PI-HBr Tablet B. To evaluate the safety and tolerability of two tablet formulations administered as a single oral dose of TBPM-PI-HBr in healthy adult subjects. To evaluate the safety and tolerability of TBPM-PI-HBr administered as Tablet B under fasted and fed conditions. | TBPM PK parameters following administration of TBPM-PI-HBr Tablet B under fasted and fed conditions: AUC0-inf, AUC0-t, Cmax, Tmax, t½, and Kel. Incidence of TEAEs, postbaseline changesin 12-lead electrocardiograms (ECGs), vital sign measurements, and clinical laboratory tests up to 24 hours following each dose of TBPM-PI-HBr. |

This was an open-label, randomized, single-dose, semi-replicate, 3-sequence, 4-period crossover, BE (under fasted conditions) and food-effect study. Thirty-six (36) healthy, adult male and female subjects were enrolled. Screening of subjects occurred within 28 days prior to the first dosing. Subjects were randomized to one of three sequences (BA1A2C, A1BA2C, or A1A2BC), according to the treatments described as follows. On Day 1 of Periods 1 through 3, subjects in each sequence received a single oral dose of TBPM-PI-HBr, as either Tablet A (the reference batch) under fasted conditions (Treatment A) or Tablet B under fasted conditions (Treatment B). On Day 1 of Period 4, subjects in all treatment sequences received a single oral dose of TBPM-PI-HBr as Tablet B under fed conditions (Treatment C). Each subject received Treatment A (A1 and A2) in two separate periods, and Treatments B and C on only one occasion each. There was a washout period of at least 7 days between doses. Whole blood sampling for TBPM PK was conducted predose and up to 24 hours post dose, according to the schedule outlined in the study Protocol. Safety and tolerability were monitored throughout the study by repeated clinical and laboratory evaluations. Treatment groups are set forth in Table 14, below.

Subjects were randomized to treatment sequences to minimize assignment bias. A crossover design was used to reduce the residual variability for the BE portion as every subject acted as their own control. A crossover design reduced variability caused by subject-specific factors, thereby increasing the ability to discern differences because of formulation. A semi-replicate design (in Periods 1 through 3) was used to assess the within-subject variability of the Tablet A formulation (reference, Treatment A). The confidence limit of acceptance may also have been scaled using the statistical scaling approach analysis (Davit, B M et al., AAPS J. (2012) 14(4): 915-924; Haidar, S H et al., AAPS J. (2008) 10(3): 450-454) if the within-subject standard deviation (SD) of the reference formulation was ≥29.4%, otherwise the standard 80.00% to 125.00% BE limits were applied. The washout period of 7 days between dosing periods was considered sufficient to prevent carryover effects of the preceding treatment, based on the TBPM t½ of approximately 1 hour. Film-coated tebipenem pivoxil hydrobromide tablet, 300 mg Tablet B and Tablet A were Manufactured by Meiji Seika Pharma Co., Ltd. The same lot numbers were used during the entire course of the study.

TABLE 14

| ARM Name | Treatment A[a] | Treatment B | Treatment C |
|---|---|---|---|
| Intervention Description | 600 mg (2 × 300 mg tablets) Tablet ATBPM-PI-HBr administered under fastedconditions | 600 mg (2 × 300 mg tablets) Tablet B TBPM-PI-HBr administered underfasted conditions | 600 mg (2 × 300 mg tablets) Tablet B TBPM-PI-HBr administered under fed conditions |
| Dose Formulation | Tablets | Tablets | Tablets |
| Unit Dose Strength(s) | 300 mg | 300 mg | 300 mg |
| Route of Administration | Oral | Oral | Oral |
| Use | Tablet A | Tablet B | Tablet B |
| IMP | IMP | IMP | IMP |
| Sourcing | Provided by the Sponsor. | Provided by the Sponsor. | Provided by the Sponsor. |
| Packaging and Labeling | Study intervention wasprovided in a high-density polyethylene (HDPE) bottle. Each HDPE bottle was labelledas per country requirement. | Study intervention wasprovided in a HDPE bottle. Each HDPE bottle was labelled as per country requirement. | Study intervention wasprovided in a HDPE bottle. Each HDPE bottle was labelled as per country requirement. |

[a]Treatment A was adminstered in Periods 1 and 2 as Treatments A1 and A2, respectively.

IMP = investigational medical product.

The appropriate noncompartmental PK parameters were calculated from the plasma TBPM concentration-time data using validated Phoenix® WinNonlin® Version 8.1. Actual sample times were used in the calculations of the PK parameters. The calculation of the actual time was in respect to the dose administration time of TBPM-PI-HBr on Day 1 of the given study period. All PK parameters included in the protocol are listed in TABLE 15, and are defined as appropriate for study design.

TABLE 15

Noncompartmental Pharmacokinetic Parameters Calculated for TBPM

| Cmax | Cmax | Maximum observed concentration | Taken directly from bioanalytical data |
|---|---|---|---|
| Tmax | Tmax | Time to reach $C_{max}$; if the maximum value occurred at more than one time point, $T_{max}$ was defined as the first time point with this value | Time of the blood draw which was associated with the $C_{max}$ |
| Tlast | Tlast | Time to reach last observed (quantifiable,nonzero) plasma concentration ($C_{last}$) | Time of the blood draw which was associated with the $C_{last}$ |
| Kel | Kel | Apparent first-order terminal eliminationrate constant | Calculated by linear least squares regression analysis using the maximum number of points in the terminal log linearphase (e.g., 3 or more nonzero plasma concentrations) |
| t½ | t½ | Apparent first-order terminal eliminationhalf-life | $t_{1/2} = 0.693/K_{el}$ |

Concentration values and PK parameters for subjects who experienced vomiting at or prior to 2-times median $T_{max}$ value for that group were reported, to the extent possible, but excluded from descriptive statistics and statistical analysis and were also presented in individual concentration versus time figures only.

Predose plasma TBPM concentrations below the limit of quantitation (BLQ) were treated as zero, and post dose BLQ plasma TBPM concentrations were treated as missing for all PK calculations. Profiles were considered to have terminated after 2 or more consecutive BLQ values; any subsequent quantifiable concentrations were excluded from the descriptive statistics and the calculation of PK parameters.

The $K_{el}$ was determined using linear regressions composed of at least 3 data points, not including $C_{max}$. The $K_{el}$ was not to be assigned if 1) the terminal elimination phase was not apparent, or 2) if the $R_2$ value was less than 0.75. Wherever the resulting $t_{1/2}$ was more than half as long as the sampling interval, the $K_{el}$ values and associated parameters ($t_{1/2}$, $AUC_{0-inf}$ and $AUC_{\%extrap}$) may not have been presented, as judged appropriate and in accordance with Celerion SOPs (there were no cases with ty greater than half the sampling interval). Wherever $AUC_{\%extrap}$ was ≥20%, the $K_{el}$ values and associated parameters ($t_{1/2}$, $AUC_{0-inf}$ and $AUC_{\%extrap}$) were to be reported, but excluded from descriptive statistics and statistical analysis (there were no cases of $AUC_{\%extrap} \geq 20\%$).

Drug Concentration Measurements

Whole blood samples for the determination of TBPM were collected from all subjects at the following time points in each study period: predose and at 0.25, 0.5, 0.75, 1, 1.25, 1.5, 2, 3, 4, 6, 8, 10, 12, 16, and 24 hours post dose.

All concentration data were included in the calculation of the individual PK parameters, the individual concentration-time plots (based on actual sample times), and in the mean concentration-time plots (based on nominal sample times). All deviations and excluded data are provided and discussed in the CSR.

Bioanalytical Methods

Blood concentrations of TBPM were determined using a validated liquid chromatography-tandem \ mass spectrometry (LC-MS/MS) method at Charles River Laboratories (Shrewsbury, MA). TBPM blood concentrations were converted to plasma concentrations using the following equation:

TBPM plasma concentration=reported blood concentration×3.6.

Where 3.6 represents the product of 1/plasmatocrit (average plasmatocrit value of 0.55) value of 1.8 and a dilution factor of 2 by addition of 1:1 isopropyl alcohol:blood volume. Isopropyl alcohol was added as a stabilizer during blood sample collections to prevent conversion of TBPM-PI to TBPM post sample collection.

Pharmacokinetic Analysis—Data Summarization and Presentation

All TBPM PK concentrations and/or PK parameters descriptive statistics were generated using SAS® Version 9.4. The plasma concentrations of TBPM were listed and summarized by treatment (A1, A2, B, and C) and time point for all subjects in the PK Population. Plasma concentrations of TBPM were presented with the same level of precision as received from the bioanalytical laboratory. Summary statistics, including sample size (n), arithmetic mean (Mean), SD, coefficient of variation (CV %), standard error of the mean (SEM), minimum, median, and maximum were calculated for all nominal concentration time points. Subjects excluded from the PK Population were included in the concentration listings, but were excluded from the summary statistics and noted as such in the tables. All BLQ values were presented as "BLQ" in the concentration listings and footnoted accordingly. All plasma concentrations that were BLQ were designated a value of zero for the purposes of summaries of concentration-time data. For all post dose time points, if more than 50% of values were BLQ or the mean was BLQ, the mean, SD, CV %, and SEM were shown as not calculable, and the minimum, median, and maximum (if applicable) values were shown as being BLQ.

Mean and individual plasma concentration-time profiles for TBPM were presented on linear and semi-log scales. Linear mean plots were presented with and without SD. For the concentration-time points where the SD was not calculable, only mean values were presented. Plasma TBPM PK parameters were listed and summarized by treatment for all subjects in the PK Population. Summary statistics (n, mean, SD, CV %, SEM, minimum, median, maximum, geometric mean [Geom Mean], and geometric CV % [Geom CV %]) were calculated for plasma TBPM PK parameters. Subjects excluded from the PK Population were not listed in the PK parameter tables.

Statistical Analysis of Pharmacokinetic Parameters

Bioequivalence

Depending on the within-subject variability, either a two one-sided test procedure or a reference-scaled average BE Approach was planned to assess the BE for the $AUC_{0-t}$, $AUC_{0-inf}$ and $C_{max}$ of TBPM-PI-HBr. Within-subject variability for a specific PK parameter of the reference product was first determined. The comparison of the test and reference PK parameters ($AUC_{0-t}$, $AUC_{0-inf}$ and $C_{max}$) was conducted using an analysis of variance (ANOVA) model with PROC MIXED of SAS Version 9.4. The analysis was performed on natural log (ln)-transformed PK parameters. The statistical model contained fixed effects of sequence, treatment, and period and a random effect of subject modeled with a no diagonal factor analytic (FA0(2)) covariance structure.

Data from Treatments A (A1 and A2) and B were used to perform the analysis.

Point estimates and 90% confidence intervals (CIs) were constructed for the relevant contrasts from the ANOVA models detailed above. The point estimate and 90% CI were back-transformed to give estimates of the ratio of the geometric least-squares means (LSMs) and corresponding 90% CI. Estimated geometric means were also presented for each treatment. The geometric mean ratios (GMRs) were expressed as a percentage of test (Treatment B) relative to the reference treatment (Treatment A).

Bioequivalence was concluded if one of the following conditions was satisfied for each PK parameter $AUC_{0-t}$, $AUC_{0-inf}$ and $C_{max}$:

a. If $W_R\sigma<0.294$ (intra-subject CV %<30%), the two one-sided tests procedure was used to determine BE for the individual PK parameter(s). For a given PK parameter, BE was concluded if the 90% CI of the GMR of the test to the reference formulation (Treatment A) fell within 80.00% to 125.00%.

b. If $W_{REx}\sigma \geq 0.294$ (intra-subject CV %≥30%), the reference-scaled procedure was used to determine BE for the individual PK parameter(s).

For a given PK parameter, BE was concluded if:
1. the GMR of the test (Treatment B) to the reference formulation (Treatment A) lay within 80.00% to 125.00%, and
2. the 95% upper confidence bound of the linearized scale difference $$(LSM_{Test}-LSM_{Ref})^2-\theta(\sigma_{wr})^2$$

was less than or equal to zero (≤0), where $$\theta=[\ln(1.25)/0.25]^2$$

represents the scaled average BE limit.

Food Effect

To assess the potential food-effect, an ANOVA was performed on the ln-transformed $AUC_{0-t}$, $AUC_{0-inf}$ and $C_{max}$. The ANOVA model included treatment as a fixed effect (for Treatments B and C only) and subject as a random effect. Each ANOVA included calculation of LSMs as well as the difference between treatment LSMs.

Point estimates and 90% CIs were constructed for the relevant contrasts from the ANOVA models detailed above. The point estimate and 90% CI were back-transformed to give estimates of the ratios of the geometric LSM and corresponding 90% CI. Estimated geometric means were also presented for the fed and fasted state. The GMRs were expressed as a percentage of the fed (Treatment C) relative to the fasted state (Treatment B).

Data from Treatments B and C were used to perform the analysis. For Treatment A, the summarization was performed by Treatment A1 and Treatment A2 separately and then combined Treatment A.

Determination of Sample Size

A total of 36 subjects were enrolled for this study. This was based upon a within-subject SD (logscale) of 0.3 for AUC, based upon previous studies, and assuming the residual variability would be 0.75 times the within-subject variability due to the use of a 3-period crossover design for the BE portion of this study. Using this estimate of variability, a study including 36 subjects would have >90% power to show BE to traditional BE limits of 0.8 to 1.25 assuming no true difference in the test and reference formulation. Given that $C_{max}$ appeared highly variable, with SD (log scale) >0.4, a replicate design was utilized where the reference product was repeated in two treatment periods. This allowed a reference-scaled BE limit to be used for AUC or $C_{max}$ when the within-subject SD (log scale) was >0.294. The sample size was considered sufficient to evaluate the magnitude of the potential food effect.

All 36 subjects completed the study and were included in the PK and safety analyses, with the following exception. The data for Subject 105-007-0026 were excluded from the summaries and statistical comparisons of PK parameters for Tablet B administered under fed conditions (Treatment C), because the subject vomited within 2-times the median $T_{max}$.

Disposition of Subjects

A total of 36 subjects entered the study and were randomized to one of the following three treatment sequences: A1A2BC, A1BA2C, or BA1A2C. All 36 subjects completed study treatments as per protocol. A summary of disposition is in TABLE 16.

TABLE 16

| Disposition | Randomized Treatment Sequen | | | |
| --- | --- | --- | --- | --- |
| | A1A2BC | A1BA2C | BA1A2C | Overall |
| Enrolled | 12 (100%) | 12 (100%) | 12 (100%) | 36 (100%) |
| Completed | 12 (100%) | 12 (100%) | 12 (100%) | 36 (100%) |
| Discontinued Early | 0 (0%) | 0 (0%) | 0 (0%) | 0 (0%) |

Figure 4:
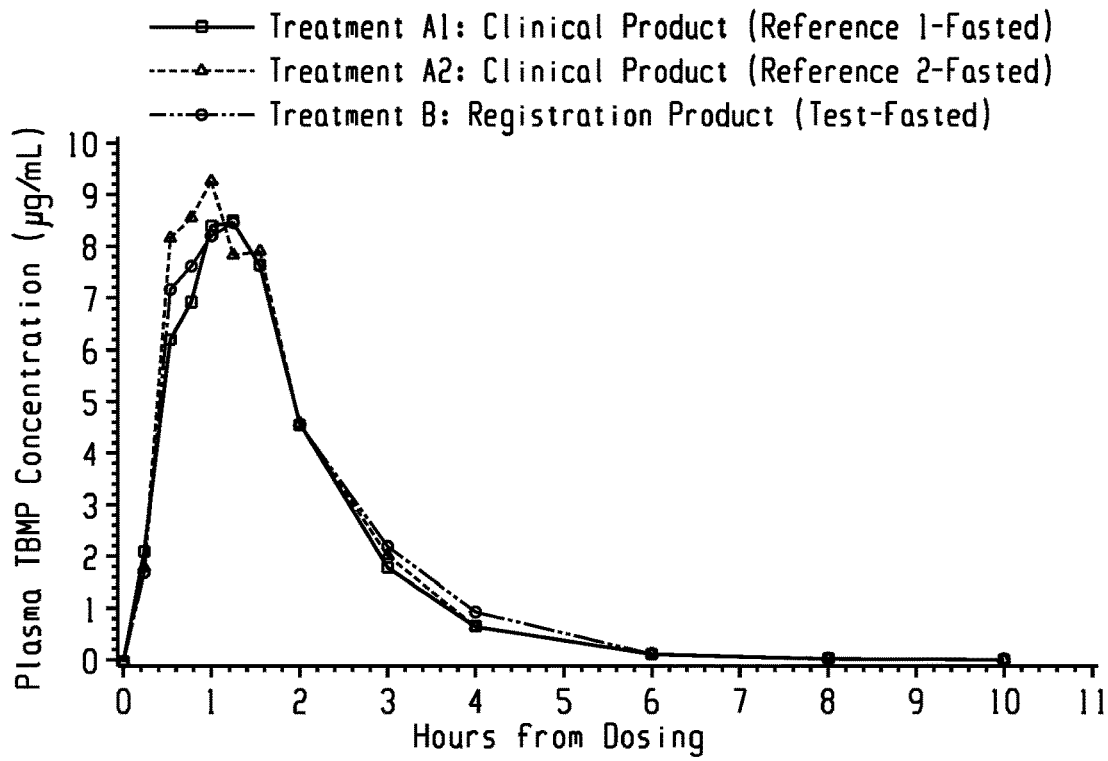
FIG. 4. Arithmetic Mean Plasma TBPM Concentration Versus Time Profiles Following Administration of 600 mg Tablet A, Ex. 15 and Tablet B, Ex. 15 (Treatment B) TBPM-PI-HBr (Linear Scale) (Pharmacokinetic Population). The x-axis was truncated after 10 hours, because, for all subsequent timepoints, greater than 50% of the values were BLQ (<0.0072 μg/mL).
Figure 5:
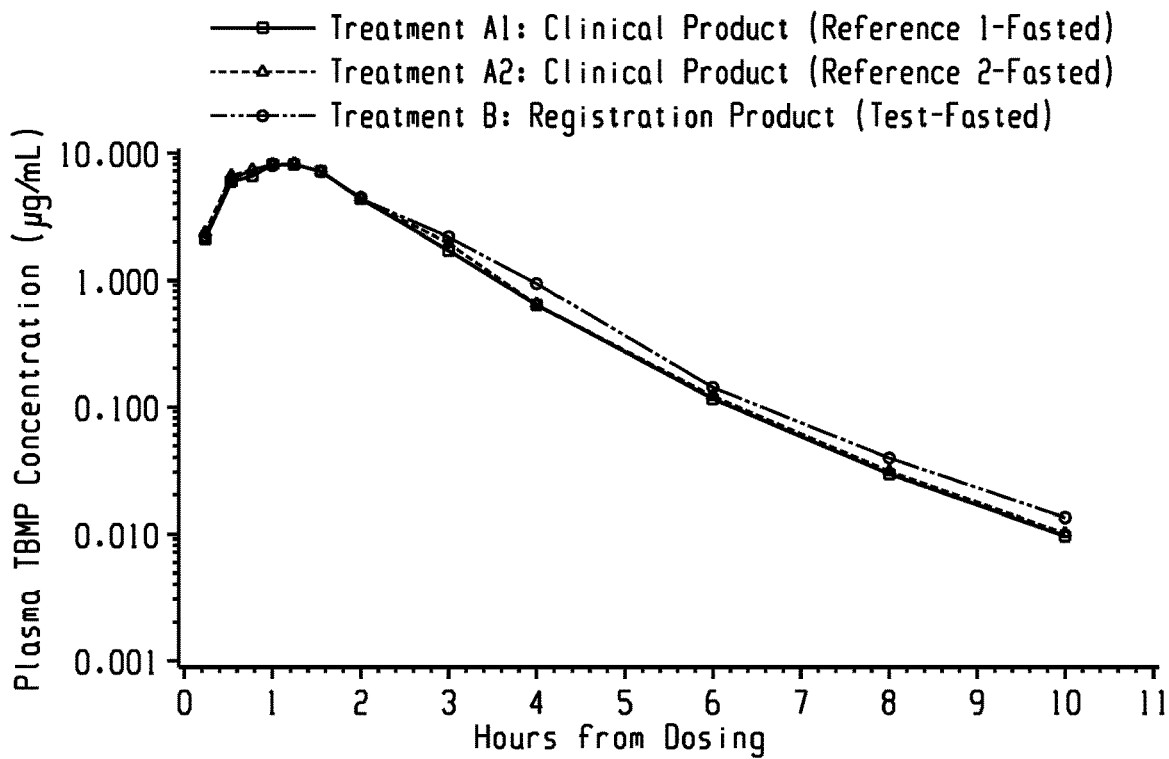
FIG. 5. Arithmetic Mean Plasma TBPM Concentration Versus Time Profiles Following Administration of 600 mg Tablet A (Treatments A1 and A2) and Tablet B (Treatment B) TBPM-PI-HBr (Semi-Log Scale) (Pharmacokinetic Population). The x-axis was truncated after 10 hours, because, for all subsequent timepoints, greater than 50% of the values were BLQ (<0.0072 μg/mL).

Treatment A1 First administration of 600 mg (2 × 300 mg tablets) Tablet ATBPM-PI-HBr administered at Hour 0 on Day 1, under fasted conditions
Treatment A2: Second administration of 600 mg (2 × 300 mg tablets) Tablet ATBPM-PI-HBr administered at Hour 0 on Day 1, under fasted conditions
Treatment B: 600 mg (2 × 300 mg tablets) Tablet B TBPM-PI-HBr administered at Hour 0 on Day 1, under fasted conditions
Treatment C: 600mg (2 × 300 mg tablets) Tablet B TBPM-PI-HBr administered at Hour 0 on Day 1 under fed conditions Mean plasma TBPM concentration-time profiles following the administration of Tablet A or Tablet B under fasted conditions are presented on a linear scale in FIG. 4 and on a semi-log scale in FIG. 5.

Plasma TBPM concentrations were quantifiable by the first postdose sample time (0.25 hours) for all but two subject profiles following the first administration of Tablet A (Treatment A1), all profiles following the second administration of Tablet A (Treatment A2), and all but one subject profile following Tablet B (Tablet B, Treatment B) administered under fasted conditions. Based on FIG. 4, Peak mean concentrations were comparable for the two administrations of Tablet A and for Tablet B under fasted conditions, occurring at 1 to 1.25 hours post dose for each of the three treatments. There were multiple occurrences of double peak-like patterns in the individual plasma.

In the terminal phase, mean plasma TBPM concentrations were also comparable for the two administrations of Tablet A and Tablet B under fasted conditions.

TBPM concentrations remained quantifiable for the majority (>50%) of the subjects through 10 hours post dose, and the majority of the profiles were BLQ (<0.0072 μg/mL) at 12 hours post dose, for each administration of Tablet A and Tablet B. All plasma TBPM concentrations were BLQ by 16 hours post dose for each administration of Tablet A and for Tablet B, with one exception. There was one sporadic quantifiable concentration (0.00749 μg/mL) at 24 hours postdose for Subject 105-007-0021 following Tablet B under fasted conditions; however, the profile was considered to have terminated after the two consecutive BLQ concentrations at 12 and 16 hours post dose.

Three (3) samples were re-assayed due to anomalous results: (1) Subject 105-007-0006 at Hours 16 and 24 for Treatment A1, (2) Subject 105-007-0020 at Hour 12 for Treatment A2.

Figure 6:
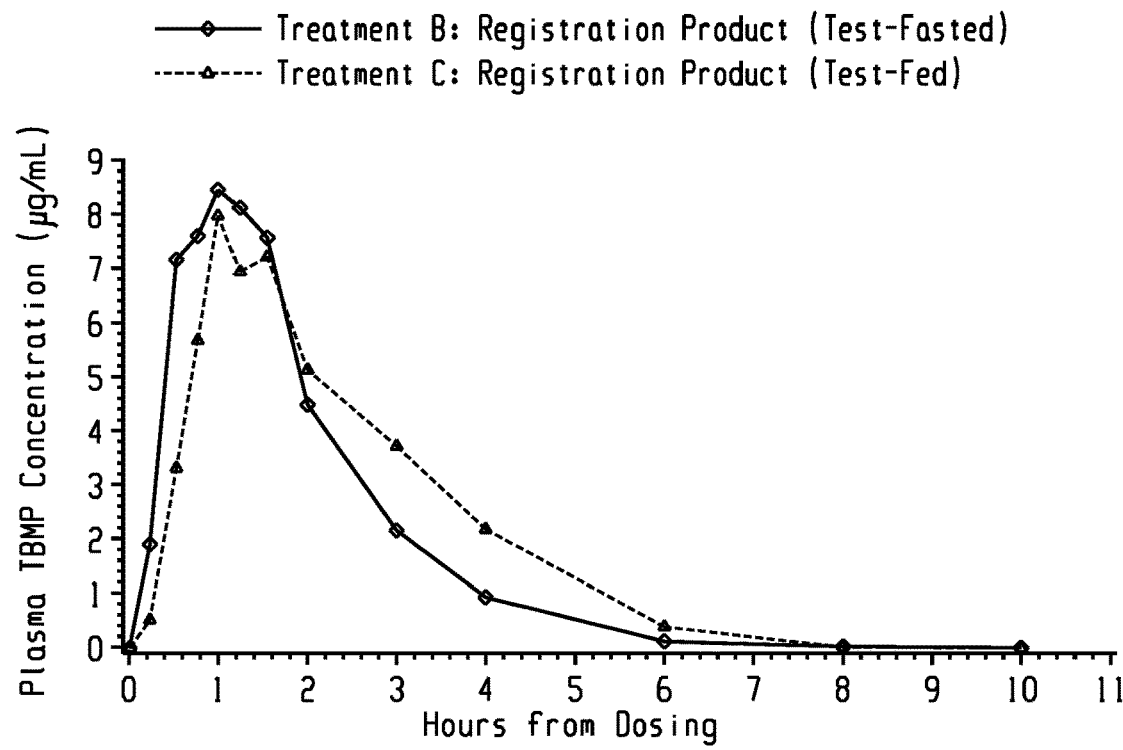
FIG. 6: Arithmetic Mean Plasma TBPM Concentration Versus Time Profiles Following Administration of 600 mg Tablet B TBPM-PI-HBr Under Fasted (Treatment B) and Fed (Treatment C) Conditions (Linear Scale) (Pharmacokinetic Population). The x-axis was truncated after 10 hours, because, for all subsequent timepoints, greater than 50% of the values were BLQ (<0.0072 μg/mL).
Figure 7:
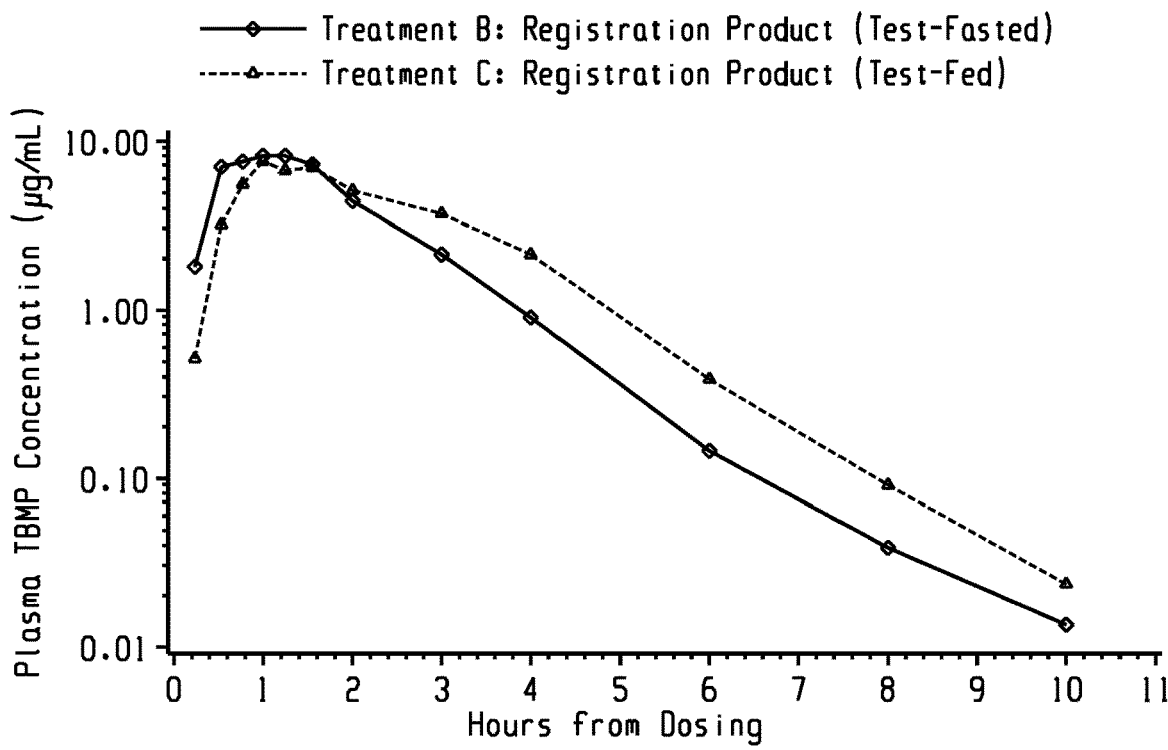
FIG. 7. Arithmetic Mean Plasma TBPM Concentration Versus Time Profiles Following Administration of 600 mg Tablet B TBPM-PI-HBr Under Fasted (Treatment B) and Fed (Treatment C) Conditions (Semi-Log Scale) (Pharmacokinetic Population). The x-axis was truncated after 10 hours, because, for all subsequent timepoints, greater than 50% of the values were BLQ (<0.0072 µg/mL).

Mean plasma TBPM concentration-time profiles following the administration of Tablet B under fasted or fed conditions are presented on a linear scale in FIG. 6 and on semi-log scale in FIG. 7.

The rate of absorption appeared to be slower and for an extended interval for Tablet B administered under fed (Treatment C) relative to fasted (Treatment B) conditions, with concentrations in fed subjects BLQ at 0.25 hours post dose for 13 subjects, and remaining BLQ for four subjects and one subject at 0.5 and 0.75 hours post dose, respectively. Based on FIG. 6, while peak mean concentrations were comparable and occurred at 1 hour post dose for Tablet B administered under both fasted and fed conditions, there was a second apparent peak mean concentration for the fed treatment, reflective of a slightly delayed/lower peak for a number of subjects.

Mean plasma TBPM concentrations were higher throughout the elimination phase for Tablet B administered under fed relative to fasted conditions, though the slope in the terminal portion of the curves appeared to be comparable between the two treatments. As was observed for Tablet B under fasted conditions, concentrations remained quantifiable for the majority of subjects through 10 hours post dose, and the majority of the profiles were BLQ at 12 hours post dose, for Tablet B administered under fed conditions. All plasma TBPM concentrations were BLQ by 16 hours post dose for Tablet B under fed conditions. A summary of the tebipenem pivoxil PK parameters is listed in TABLE 17.

TABLE 17

Summary of Plasma TBPM Pharmacokinetic Parameters Following Administration of 600 mg TBPM-PI-HBr (Pharmacokinetic Population)

| Pharmacokinetic Parameters | Treatment A1 [n = 36] | Treatment A2 [n = 36] | Treatment B [n = 36] | Treatment C [n = 35] |
|---|---|---|---|---|
| $AUC_{0-t}$ (μg*hr/mL) | 16.17(28.3) | 16.92(38.1) | 16.88(34.3) | 18.76(39.6) |
| $AUC_{0-inf}$ (μg*hr/mL) | 16.9(28.3) | 16.94(38.0) | 16.91(34.3) | 18.78(39.5) |
| $C_{max}$ (μg*hr/mL) | 10.54(35.8) | 10.57(40.7) | 10.09(40.5) | 8.841(58.3) |
| $T_{max}$ (hr) | 1.02(0.50,2.0) | 1.00(0.50,2.0) | 1.25(0.49,2.0) | 1.49(0.74,4.0) |
| $T_{1/2}$ (hr) | 1.157 ± 0.2156 | 1.172 ± 0.2226 | 1.189 ± 0.2219 | 1.008 ± 0.1332 |

Treatment A1: First administration of 600 mg (2 × 300 mg tablets) Tablet ATBPM-PI-HBr administered at Hour 0 on Day 1, under fasted conditions
Treatment A2: Second administration of 600 mg (2 × 300 mg tablets) Tablet ATBPM-PI-HBr administered at Hour 0 on Day 1, under fasted conditions
Treatment B: 600 mg (2 × 300 mg tablets) Tablet B TBPM-PI-HBr administered at Hour 0 on Day 1, under fasted conditions
Treatment C: 600 mg (2 × 300 mg tablets) Tablet B TBPM-PI-HBr administered at Hour 0 on Day 1, under fed conditions
The data for Subject 105-007-0026 were excluded from the summary statistics for Treatment C, because the subject vomited within 2-times the median Tmax
AUCs and Cmax values are presented as geometric mean (geometric CV %).
Tmax values are presented as median (minimum, maximum).
t½ values are presented as arithmetic mean ±SD.

Plasma TBPM PK parameters were comparable between the two administrations of Tablet A under fasted conditions (Treatments A1 and A2).

Geometric mean AUC0-t, AUC0-inf, and Cmax values were comparable for Tablet A and Tablet B (Treatment B) administered under fasted conditions. The median Tmax was approximately 1 hour for each administration of Tablet A and 1.25 hours for Tablet B under fasted conditions, with a comparable range (minimum to maximum) of individual Tmax values observed. Mean t½ values were also comparable between each administration of Tablet A and Tablet B under fasted conditions, at approximately 1.2 hours.

Geometric mean AUC0-t and AUC0-inf values were comparable for Tablet B administered under fasted and fed (Treatment C) conditions, when variability was taken into consideration; however, the geometric mean Cmax was lower under fed relative to fasted conditions. The median Tmax was slightly delayed for Tablet B under fed conditions at approximately 1.5 hours, with a later range (minimum to maximum) of individual Tmax values under fed relative to fasted conditions. The mean t½ was similar for Tablet B under fasted and fed conditions.

The summary of the statistical comparisons of TBPM PK parameters following Tablet B versus Tablet A under fasted conditions is presented in TABLE 18.

TABLE 18

Summary of the Statistical Comparisons of Plasma TBPM Pharmacokinetic Parameters
Following Administration of 600 mg Tablet B (Treatment B) Versus Tablet A Batch
(Treatment A) TBPM-PI-HBr (Pharmacokinetic Population)

| Parameter | Treatment B Geometric LSMs | n | Treatment A Geometric LSMs | n | GMR (%) | 90% Confidence Interval | Intrasubject CV % Treatment A |
|---|---|---|---|---|---|---|---|
| AUC0-t (μg * hr/mL) | 16.88 | 36 | 16.54 | 72 | 102.10 | 96.86-107.61 | 20.8 |
| AUC0-inf (μg * hr/mL) | 16.91 | 36 | 16.56 | 72 | 102.09 | 96.86-107.59 | 20.8 |
| Cmax (μg/mL) | 10.09 | 36 | 10.55 | 72 | 95.59 | 87.07-104.94 | 29.4 |
| AUC0-t (μg * hr/mL) | 16.88 | 36 | 16.54 | 72 | 102.10 | 96.86-107.61 | 20.8 |

Treatment B: 600 mg (2 × 300 mg tablets) Tablet B TBPM-PI-HBr administered at Hour 0 on Day 1, under fasted conditions (test)
Treatment A: 600 mg (2 × 300 mg tablets) Tablet A TBPM-PI-HBr administered at Hour 0 on Day 1, under fasted conditions (reference)
Parameters were ln-transformed prior to analysis.
Geometric least-squares means (LSMs) are calculated by exponentiating the LSMs derived from the ANOVA.
Geometric Mean Ratio (GMR) = 100 × (test/reference)
Intra-subject CV % = 100 × (square root (exp[residual] − 1)), where residual = Residual variance for the treatment from ANOVA.
The BE assessment approach was Two One-Sided Tests Procedure and the BE acceptance bound is (80.00%, 125.00%) when reference formulation intra-subject CV % <30%.

Based on the statistical comparisons of ln-transformed plasma TBPM $AUC_{0-t}$, $AUC_{0-inf}$, and $C_{max}$, Tablet B was bioequivalent to Tablet A administered under fasted conditions, as the 90% CIs of the GMRs for each parameter were within the 80.00% to 125.00% BE limits (with intra-subject CV %<30% in the reference formulation for each parameter comparison). The GMRs were close to unity at approximately 102% for AUCs and 96% for $C_{max}$ were supportive of this conclusion.

The summary of the statistical comparisons of TBPM PK parameters following Tablet B administered under fed versus fasted conditions is presented in TABLE 19.

TABLE 19

Summary of the Statistical Comparisons of Plasma
TBPM Pharmacokinetic Parameters Following Administration of
600 mg TBPM-PI-HBr Tablet B Under Fed (Treatment C) Versus Fasted (Treatment B)
Conditions (Pharmacokinetic Population).

| Parameter | Treatment C Geometric LSMs | n | Treatment B Geometric LSMs | n | GMR (%) | 90% Confidence Interval |
|---|---|---|---|---|---|---|
| AUC0-t (μg * hr/mL) | 18.59 | 35 | 16.88 | 36 | 110.12 | 101.78-119.14 |
| AUC0-inf (μg * hr/mL) | 18.61 | 35 | 16.91 | 36 | 110.10 | 101.77-119.11 |
| Cmax (μg/mL) | 8.811 | 35 | 10.09 | 36 | 87.34 | 74.75-102.05 |

Treatment C: 600 mg (2 × 300 mg tablets) Tablet B TBPM-PI-HBr administered at Hour 0 on Day 1, under fed conditions (test)
Treatment B: 600 mg (2 × 300 mg tablets) Tablet B TBPM-PI-HBr administered at Hour 0 on Day 1, under fasted conditions (reference)
The data for Subject 105-007-0026 were excluded from the statistical comparisons for Treatment C, because the subject vomited within 2-times the median Tmax.
Parameters were ln-transformed prior to analysis.
Geometric least-squares means (LSMs) are calculated by exponentiating the LSMs derived from the ANOVA.
Geometric mean Ratio (GMR) = 100 × (test/reference).
The no food effect acceptance bound is 80.00%, 125.00%).

Based on the statistical comparisons of ln-transformed plasma TBPM PK parameters following Tablet B administered under fed versus fasted conditions, food was determined not to influence overall TBPM exposure, as the 90% CIs of the GMRs for $AUC_{0-t}$ and $AUC_{0-inf}$ were within the standard equivalence limits of 80.00% to 125.00%. The GMRs for AUCs were approximately 110%. Food did have a slight effect on TBPM peak exposure, as the lower bound of the 90% CI of the GMR for $C_{max}$ (74.75%) fell below the 80.00% to 125.00% limits. The GMR for $C_{max}$ indicated food decreased TBPM peak exposure by approximately 13%.

Pharmacokinetic Conclusions

The Tablet B batch of TBPM-PI-HBr was bioequivalent to Tablet A (90% CIs for TBPM $AUC_{0-t}$, $AUC_{0-inf}$, and $C_{max}$ were within the 80.00% to 125.00% BE limits) when administered under fasted conditions. An FDA standard high-fat/high-calorie meal had no meaningful effect on the total plasma exposure of TBPM after administration of Tablet B of TBPM-PI-HBr, as overall exposure (based on $AUC_{0-t}$ and $AUC_{0-inf}$) was comparable when administered under fed compared to fasted conditions.

TBPM peak plasma concentration ($C_{max}$) was approximately 13% lower after administration of Tablet B of TBPM-PI-HBr under fed compared to fasted conditions.

Pharmacokinetics

Tablet B was bioequivalent to Tablet A administered under fasted conditions, as the 90% CIs of the GMRs for each parameter were within the 80.00% to 125.00% BE limits (with within-subject SD less than 0.294 or intra-subject CV % less than 30% for each parameter comparison in the reference formulation). The GMRs of approximately 102% for AUCs and 96% for $C_{max}$ were supportive of this conclusion. The mean $t_{1/2}$ values and the range (minimum to maximum) of individual $T_{max}$ values were also comparable between each administration of Tablet A and Tablet B under fasted conditions. Based on the statistical comparisons of ln-transformed plasma TBPM PK parameters following Tablet B administered under fed versus fasted conditions, food was determined not to have an effect on overall TBPM exposure, as the GMRs and 90% CIs of the GMRs for $AUC_{0-t}$ and $AUC_{0-inf}$ were within the default equivalence limits of 80.00% to 125.00% (with GMRs of approximately 110%). However, food was determined to affect TBPM peak exposure, as the lower bound of the 90% CI of the geometric LSMs for $C_{max}$ fell below the 80.00% to 125.00% limits. The GMR for $C_{max}$ indicated food decreased TBPM peak plasma levels ($C_{max}$) by approximately 13%. Moreover, the median and range (minimum to maximum) of individual $T_{max}$ values were slightly delayed and mean profiles showed a slower and extended absorption phase for Tablet B under fed relative fasted conditions. Mean $t_{1/2}$ values were comparable between the two treatment conditions. As noted in McEntee 2019, efficacy of TBPM-PI-HBr is dependent on TBPM AUC which is unaffected by food, and only a minor decrease in $C_{max}$ (13%) was observed. Moreover, food neither affected the safety profile of TBPM-PI-HBr nor did the decrease TBPM $C_{max}$ pose a safety concern in this study. Therefore, the effect of food on TBPM PK may not be clinically relevant.

Pharmacokinetics

Tablet B of TBPM-PI-HBr was bioequivalent to the Tablet A (the reference drug product batch, 90% CIs for TBPM $AUC_{0-t}$, $AUC_{0-inf}$ and $C_{max}$ were within the 80.00% to 125.00% BE limits) when administered under fasted conditions. An FDA standard high-fat/high-calorie meal had no meaningful effect on the total plasma exposure of TBPM after administration of Tablet B of TBPM-PI-HBr, as overall exposure (based on $AUC_{0-t}$ and $AUC_{0-inf}$) was comparable when administered under fed compared to fasted conditions. TBPM peak plasma concentration ($C_{max}$) was approximately 13% lower after administration of Tablet B of TBPM-PI-HBr under fed compared to fasted conditions.

What is claimed is:

1. A tebipenem pivoxil HBr tablet core, consisting of at least 70% w/w tebipenem pivoxil HBr;
    15-25% w/w of a binder/diluent, wherein the binder/diluent is microcrystalline cellulose;
    0.5 to 2% w/w of a disintegrant, wherein the disintegrant is crospovidone;
    0.5 to 2% w/w of a glidant, wherein the glidant is silicon dioxide; and
    0.5 to 2% w/w of magnesium stearate.

2. The tebipenem pivoxil HBr tablet core of claim 1, wherein the diluent/binder is microcrystalline cellulose, grade PH-101.

3. The tebipenem pivoxil HBr tablet core of claim 1, wherein the disintegrant is crospovidone XL-10.

4. The tebipenem pivoxil HBr tablet core of claim 1, wherein the glidant is colloidal silicon dioxide, grade 200.

5. The tebipenem pivoxil HBr tablet core of claim 1, consisting of
    15-25% w/w of microcrystalline cellulose, grade PH101;
    0.5 to 2% w/w of crospovidone XL-10;
    0.5 to 2.0% w/w of colloidal silicon dioxide, grade 200; and
    0.5 to 2% w/w of magnesium stearate.

6. The tebipenem pivoxil HBr tablet core of claim 1, wherein the fraction of tebipenem pivoxil HBr particles less than 45 μm is between 18% and 42%.

7. The tebipenem pivoxil HBr tablet core of claim 1, exhibiting greater than 90% dissolution in less than 5 minutes in 500 ml pH 5 aqueous buffered medium, 37±0.5° C., at paddle speed 50 rpm.

8. A tebipenem pivoxil HBr tablet comprising the tablet core claim 1, coated with an immediate release coating.

9. The tebipenem pivoxil HBr tablet of claim 8, wherein the immediate release coating is an aqueous film coating.

10. The tebipenem pivoxil HBr tablet of claim 8, wherein the tablet contains 300 mg tebipenem pivoxil (in the form of tebipenem pivoxil HBr) and has a total weight of less than 500 mg.

11. A method of treating a bacterial infection or nontuberculous mycobacterial infection in a human patient, comprising administering a tebipenem pivoxil HBr tablet of claim 8 to the patient.

12. The method of claim 11, wherein the method is a method of treating a bacterial infection and the bacterial infection is a urinary tract infection.

13. The method of claim 12, wherein the bacterial infection is a Gram negative bacterial infection.

14. The method of claim 13 wherein the Gram negative infection is an *E. coli* infection, a *Klebsiella pneumoniae* infection, an *Acinetobacter baumannii* infection, a *Pseudomonas aeruginosa*, a *Neisseria gonorrhoeae* infection, or a *Yersinia pestis* infection.

15. The method of claim 11, wherein the method is a method of treating a nontuberculous mycobacterial infection and the mycobacterial infection is a *Mycobacterium ulcerans* infection or a *Mycobacterium abscessus* infection.

16. The tebipenem pivoxil HBr tablet core of claim 1, wherein the tablet core comprises tebipenem pivoxil HBr crystalline Form B.

17. The tebipenem pivoxil HBr tablet core of claim 1, where the tebipenem pivoxil HBr comprises at least 50% (w/w) tebipenem pivoxil HBr crystalline Form B.

18. A method of treating a cUTI, acute pyelonephritis, or bacteremia in a patient comprising administering a tablet core claim 16, wherein the tablet core comprises 600 mg tebipenem pivoxil (by weight of free base) and is administration is 3 times per day for at least 3 days.

19. A method of treating a cUTI, acute pyelonephritis, or bacteremia in a patient comprising administering a tablet core claim 16, wherein the patient has renal impairment with creatine clearance <20 mL/min., end-stage renal disease (ESRD), or is receiving hemodialysis (HD) one or more times per week, wherein the tablet core comprises 300 mg tebipenem pivoxil (by weight of free base) and is administered 2 or 3 times per day for at least 3 days.

20. A method of treating a bacterial infection in a patient, comprising administering the tebipenem pivoxil HBr tablet of claim 8 to the patient, wherein the bacterial infection is an *E. coli* infection and the *E. coli* comprises an extended spectrum beta-lactamase (ESBL)-producing *E. coli*, a levofloxacin resistant *E. coli*, a TMP-SMX-resistant *E. coli*, or a fluoroquinolone-resistant *E. coli*.

21. The method of claim 20, wherein the bacterial infection is a complicated urinary tract infection (cUTI) or complicated urinary tract infection with associated bacteremia.

22. The method of claim 20, wherein the bacterial infection is acute pyelonephritis or acute pyelonephritis with associated bacteremia.

23. A method of treating a Methicillin-susceptible *Staphylococcus aureus* (MSSA) infection, a Methicillin-susceptible *Staphylococcus epidermidis* (MSSE) infection in a patient, or a Methicillin-susceptible coagulase-negative staphylococci (MSCoNS) infection in a patient comprising administering a tebipenem pivoxil HBr tablet core or tablet of claim 8 to the patient.

24. The tebipenem pivoxil HBr tablet core of claim 1, consisting of
   75.2% w/w tebipenem pivoxil HBr;
   21.4% w/w microcrystalline cellulose;
   1.0% w/w crospovidone;
   1.0% w/w silicon dioxide, and
   1.3% w/w magnesium stearate.

25. The tebipenem pivoxil HBr tablet core of claim 8, consisting of
   73.0% w/w tebipenem pivoxil HBr;
   20.7% w/w microcrystalline cellulose;
   1.0% w/w crospovidone;
   1.0% w/w silicon dioxide, and
   1.3% w/w magnesium stearate
   and wherein the immediate release coating consists of
      3.0% w/w Opadry II.

* * * * *